(12) United States Patent
Schonemann et al.

(10) Patent No.: US 9,630,894 B2
(45) Date of Patent: Apr. 25, 2017

(54) ENERGY EFFICIENT METHOD AND APPARATUS FOR THE EXTRACTION OF BIOMOLECULES FROM DILUTE AQUEOUS SOLUTION

(71) Applicants: DYNASEP INC., Wilmington, DE (US); PHASEX CORPORATION, Lawrence, MA (US)

(72) Inventors: Hans Schonemann, Newburyport, MA (US); Brian Waibel, Kennett Square, PA (US); Val Krukonis, Lexington, MA (US)

(73) Assignees: DYNASEP INC., Wilmington, DE (US); PHASEX CORPORATION, Lawrence, MA (US)

( * ) Notice: Subject to any disclaimer, the term of this patent is extended or adjusted under 35 U.S.C. 154(b) by 6 days.

(21) Appl. No.: 14/426,009

(22) PCT Filed: Sep. 5, 2013

(86) PCT No.: PCT/US2013/058206
§ 371 (c)(1),
(2) Date: Mar. 4, 2015

(87) PCT Pub. No.: WO2014/039638
PCT Pub. Date: Mar. 13, 2014

(65) Prior Publication Data
US 2015/0210618 A1   Jul. 30, 2015

Related U.S. Application Data

(63) Continuation-in-part of application No. 13/801,901, filed on Mar. 13, 2013, now Pat. No. 9,029,615.

(60) Provisional application No. 61/697,003, filed on Sep. 5, 2012.

(51) Int. Cl.

| | |
|---|---|
| *C07C 29/86* | (2006.01) |
| *C07C 29/80* | (2006.01) |
| *C07C 7/10* | (2006.01) |
| *C07D 307/48* | (2006.01) |
| *C07D 307/36* | (2006.01) |
| *C07C 45/48* | (2006.01) |
| *C07C 27/34* | (2006.01) |
| *C07C 29/88* | (2006.01) |

(52) U.S. Cl.
CPC .............. *C07C 7/10* (2013.01); *C07C 27/34* (2013.01); *C07C 29/80* (2013.01); *C07C 29/86* (2013.01); *C07C 45/48* (2013.01); *C07D 307/36* (2013.01); *C07D 307/48* (2013.01); *C07C 29/88* (2013.01)

(58) Field of Classification Search
CPC .......... C07C 29/86; C07C 29/80; C07C 29/88
USPC ................................................. 568/913, 918
See application file for complete search history.

(56) References Cited

U.S. PATENT DOCUMENTS

| | | |
|---|---|---|
| 2,188,051 A | 1/1940 | Lantz |
| 2,631,966 A | 3/1953 | Francis |
| 3,939,281 A | 2/1976 | Schwengers |
| 3,969,196 A | 7/1976 | Zosel |
| 4,124,528 A | 11/1978 | Modell |
| 4,346,241 A | 8/1982 | Feldman |
| 4,379,028 A | 4/1983 | Berg et al. |
| 4,409,406 A | 10/1983 | Feldman |
| 4,454,358 A | 6/1984 | Kummer et al. |
| 4,455,198 A | 6/1984 | Zudkevitch et al. |
| 4,466,923 A | 8/1984 | Friedrich |
| 4,490,405 A | 12/1984 | von Horst et al. |
| 4,492,808 A | 1/1985 | Hagen et al. |
| 4,508,928 A | 4/1985 | Victor |
| 4,517,298 A | 5/1985 | Tedder |
| 4,520,213 A | 5/1985 | Victor |
| 4,578,525 A | 3/1986 | Brückner |
| 4,624,417 A | 11/1986 | Gangi |
| 4,692,432 A | 9/1987 | Tedder |
| 4,749,495 A | 6/1988 | Schmidt et al. |
| 4,769,112 A | 9/1988 | Wheldon |
| 4,770,780 A | 9/1988 | Moses |
| 4,842,693 A | 6/1989 | Wheldon |
| 4,865,973 A | 9/1989 | Kollerup et al. |
| 4,877,530 A | 10/1989 | Moses |
| 4,956,052 A | 9/1990 | Hirata et al. |
| 5,013,447 A | 5/1991 | Lee et al. |
| 5,028,240 A | 7/1991 | Moore et al. |
| 5,036,005 A | 7/1991 | Tedder |
| 5,084,142 A | 1/1992 | Berg et al. |

(Continued)

FOREIGN PATENT DOCUMENTS

| | | |
|---|---|---|
| CN | 1560008 | 1/2005 |
| DE | 40 41 097 | 6/1992 |

(Continued)

OTHER PUBLICATIONS

Planovskiy et al., "Protsessy i apparaty khimicheskoy teknologii", Moscow, Goskhimizdat, pp. 648, fig. 18-14, 1962.
Munson et al., "Factors Influencing Solvent Selection for Extraction of Ethanol from Aqueous Solutions", *Industrial and Engineering Chemistry Process Design and Development*, vol. 23, pp. 109-115, 1984.
Mehta et al., "A Novel Extraction Process for Separating Ethanol and Water", *Industrial and Engineering Chemistry Process Design and Development*, vol. 24, pp. 556-560, 1985.
Krukonis, *Superficial Fluid Extraction*, 2$^{nd}$ Ed., Figure 8.11, p. 173, 1994.

(Continued)

*Primary Examiner* — Elvis O Price
(74) *Attorney, Agent, or Firm* — Greenblum & Bernstein, P.L.C.

(57) ABSTRACT

The present invention relates to the energy efficient and selective extraction of dilute concentrations of biomolecules, e.g., small organic compounds, e.g., one or more C2-C6 alcohols, one or more C3-C5 carboxylic acids, one or more C8-18 fatty alcohols, one or more C1-C18 dicarboxylic acids, one or more furfurals, one or more furans, one or more butanediols, one or more butadienes, and mixtures thereof, from an aqueous solution using liquid phase dimethyl ether (DME).

20 Claims, 12 Drawing Sheets

(56) References Cited

U.S. PATENT DOCUMENTS

| | | |
|---|---|---|
| 5,085,739 A | 2/1992 | Berg et al. |
| 5,160,044 A | 11/1992 | Tan |
| 5,215,902 A | 6/1993 | Tedder |
| 5,284,983 A | 2/1994 | Muto et al. |
| 5,349,084 A | 9/1994 | Shishikura et al. |
| 5,354,912 A | 10/1994 | Hwan et al. |
| 5,663,454 A | 9/1997 | Preston |
| 5,718,937 A | 2/1998 | Heidlas et al. |
| 5,932,101 A | 8/1999 | Kanel et al. |
| 6,106,720 A | 8/2000 | Kanel et al. |
| 6,569,640 B1 | 5/2003 | Castor et al. |
| 7,186,796 B2 | 3/2007 | Krukonis et al. |
| 7,537,700 B2 | 5/2009 | Kanda et al. |
| 8,101,808 B2 | 1/2012 | Evanko et al. |
| 8,263,814 B2 | 9/2012 | Waibel et al. |
| 8,409,834 B2 | 4/2013 | Burlew et al. |
| 9,029,615 B2 | 5/2015 | Schonemann et al. |
| 2003/0108493 A1 | 6/2003 | Henry et al. |
| 2009/0118540 A1 | 5/2009 | Rolandsgaard et al. |
| 2009/0171129 A1 | 7/2009 | Evanko et al. |
| 2010/0151098 A1 | 6/2010 | Catchpole et al. |
| 2010/0160659 A1 | 6/2010 | Catchpole et al. |
| 2011/0162953 A1 | 7/2011 | Xu et al. |
| 2011/0162954 A1 | 7/2011 | Xu et al. |

FOREIGN PATENT DOCUMENTS

| | | |
|---|---|---|
| DE | 102 00 226 | 8/2003 |
| EP | 1 122 259 | 8/2001 |
| JP | 62-29988 | 2/1987 |
| JP | 63-162636 | 7/1988 |
| WO | 2005/075614 | 8/2005 |
| WO | 2008/147705 | 12/2008 |
| WO | 2010/046619 | 4/2010 |

OTHER PUBLICATIONS

International Search Report for PCT/US2013/058206, mailed Feb. 13, 2014.

International Preliminary Report on Patentability for PCT/US2013/058206, issued Mar. 10, 2015.

Athanassios et al., "Multiphase High Pressure Equilibria in Ternary Aqueous Systems," *FluidPhase Equilibria*, 29, pp. 525-534, 1986.

Ennis et al., "Continuous Product Recovery by In-Situ Gas Stripping/Condensation During Solvent Production from Whey Permeate Using Clostridium Acetobutylicum," *Biotechnology Letters*, vol. 8, No. 10, pp. 725-730, 1986.

Laitinen et al., "Supercritical Fluid Extraction of 1-butanol from Aqueous Solutions," *Journal of Supercritical Fluids*, 15, pp. 245-252, 1999.

Maddox et al., "Production of Acetone-Butanol-Ethanol from Concentrated Substrates Using Clostridium acetobutylicum in an Integrated Fermentation-Product Removal Process," *Process Biochemistry*, vol. 30, No. 3, pp. 209-215, 1995.

Qureshi et al., "Recovery of Butanol from Fermentation Broth by Gas Stripping," *Renewable Energy*, 22, pp. 557-564, 2001.

Groot et al., "Butanol Recovery from Fermentations by Liquid-Liquid Extraction and D Membrane Solvent Extractions," *Bioprocess Engineering*, 5, pp. 203-216, 1990.

Offeman et al., "Solvent Extraction of Ethanol from Aqueous Solutions Using Biobased Oils, Alcohols, and Esters," *JOACS*, vol. 83, No. 2, pp. 153-157, 2006.

U.S. Appl. No. 61/697,003, filed Sep. 5, 2012.

ENERGY EFFICIENT METHOD AND APPARATUS FOR THE EXTRACTION OF BIOMOLECULES FROM DILUTE AQUEOUS SOLUTION

CROSS-REFERENCE TO RELATED APPLICATIONS

This application claims the benefit under 35 U.S.C. §119(e) of U.S. Provisional Application No. 61/697,003, filed on Sep. 5, 2012 and priority to U.S. application Ser. No. 13/801,901, filed on Mar. 13, 2013, which are hereby incorporated herein by reference in their entirety for all purposes.

FIELD OF THE INVENTION

The present invention relates to the energy efficient and selective extraction of biomolecules, e.g., small organic compounds, e.g., one or more C2-C6 alcohols, one or more C3-C5 carboxylic acids, one or more C8-18 fatty alcohols, one or more C1-C18 dicarboxylic acids, one or more furfurals, one or more furans, one or more butanediols, one or more butadienes, and mixtures thereof, from an aqueous solution, particularly aqueous solutions containing the alcohol in dilute or low concentrations, for example, fermentation broths.

BACKGROUND OF THE INVENTION

The notion of using a liquid solvent to extract lower alcohols, e.g., ethanol, from an aqueous solution has been pursued since the early 1980s. For example, in 1984, Munson and King published "Factors Influencing Solvent Selection for Extraction of Ethanol from Aqueous Solutions," Industrial and Engineering Chemistry Process Design and Development, 23, p 109-115. Munson and King examined solvents and solvent mixtures for the extraction of ethanol from dilute aqueous solutions. Results were tabulated on the basis of capacity, as represented by the distribution coefficient, and selectivity, as represented by the separation factor. Munson and King showed that an increasing distribution coefficient generally correlates with a decreasing separation factor. Thus, as the solvent become more effective for extracting ethanol, the solvent, unfortunately, becomes less effective for rejecting the water.

Previously disclosed methods of using an oil to extract ethanol from a dilute aqueous solution have proven to be energetically and economically inefficient. For example, Metha and Fraser, "A Novel Extraction Process for Separating Ethanol and Water," Industrial and Engineering Chemistry Process Design and Development, 24, 1985, p 556-560 detail a method to use light paraffin oil to extract ethanol from water. Their method leverages the ternary phase behavior of ethanol-water-paraffin oil system. The proposed process scheme requires process temperatures in the range from 30° C. to 115° C. The report does not provide the optimum process conditions. Ethanol's boiling point is 78° C. Furthermore, in order to have favorable energy input into the process, the process requires that paraffin oil travel with the discharged ethanol. Because paraffin oil is more valuable than ethanol, it is not clear that the proposed process has an economic advantage.

Numerous published methods for the extraction of ethanol require a distillation step to remove ethanol from water, which is energetically and economically inefficient, and an unnecessary additional step. For example, U.S. Pat. Nos. 4,409,406; 4,865,973; 4,770,780; 5,036,005; and 5,215,902 each disclose processes for the extraction of ethanol that require a distillation step to remove ethanol from water.

Others have also proposed using carbon dioxide as a primary extractant of ethanol from an aqueous solution. However, these methods are limited by the distribution coefficient between ethanol-water and $CO_2$ that has been measured to be on the order of 0.1 by numerous researchers, e.g., Krukonis (FIG. 8.11, p. 173, McHugh, M., Krukonis, V., Supercritical Fluid Extraction, 2nd Ed., Butterworth-Heinemann, 1994). These processes have no energy advantage over a traditional binary distillation process. See, for example, U.S. Pat. Nos. 4,842,693; 5,160,044; and 4,770,780.

SUMMARY OF THE INVENTION

The present invention provides energetically efficient and economically viable methods and systems for the concentration of biomolecules from dilute aqueous solutions. Illustrative biomolecules include small organic compounds, e.g., one or more C2-C6 alcohols, one or more C3-C5 carboxylic acids, one or more C8-18 fatty alcohols, one or more C1-C18 dicarboxylic acids, one or more furfurals, one or more furans, one or more butanediols, one or more butadienes, and mixtures thereof.

In one aspect, the invention provides an energetically efficient method for concentrating a biomolecule, e.g., a small organic compound, e.g., one or more C2-C6 alcohols, one or more C3-C5 carboxylic acids, one or more C8-18 fatty alcohols, one or more C1-C18 dicarboxylic acids, one or more furfurals, one or more furans, one or more butanediols, one or more butadienes, and mixtures thereof, from a dilute biomolecule-water solution. In some embodiments, the methods comprise:

a) mixing the dilute biomolecule-water solution with liquid phase dimethyl ether (DME), wherein the distribution coefficient for the biomolecule in a mixture of the DME and the biomolecule-water solution favors the transfer of the biomolecule from the biomolecule-water solution to the DME, thereby yielding a solution comprising a first phase and a second phase, the first phase comprising biomolecule-saturated or biomolecule-containing DME and the second phase comprising the dilute biomolecule-water solution (i.e., aqueous solution comprising unextracted biomolecule or raffinate), thereby extracting a portion of the biomolecule from the biomolecule-water solution into the DME;

b) separating the first phase comprising biomolecule-saturated DME and the second phase comprising the dilute biomolecule-water solution;

c) vaporizing the liquid phase DME in the first phase to vapor phase DME, thereby releasing the biomolecule from the DME, yielding a concentrated biomolecule-water solution;

d) recovering the vapor phase DME by condensing to liquid phase; and e) repeating steps a)-d), wherein the DME recovered in step d) is mixed with the dilute biomolecule-water solution in step a). The concentrated biomolecule-water solution comprises a greater biomolecule concentration than the biomolecule concentration in the starting biomolecule-water solution. In varying embodiments, the vaporizing and the condensing of the DME is driven by a refrigerant circuit.

In a further aspect, the invention provides methods for concentrating a biomolecule, e.g., a small organic compound, e.g., one or more C2-C6 alcohols, one or more C3-C5 carboxylic acids, one or more C8-18 fatty alcohols, one or more C1-C18 dicarboxylic acids, one or more furfurals, one or more furans, one or more butanediols, one or more butadienes, and mixtures thereof, from a dilute biomolecule-water solution. In some embodiments, the methods comprise:

a) mixing the dilute biomolecule-water solution comprising less than 10 wt. % biomolecule with liquid phase dimethyl ether (DME), wherein the distribution coefficient for the biomolecule in a mixture of the DME and the biomolecule-water solution favors the transfer of the biomolecule from the biomolecule-water solution to the DME, thereby yielding a solution comprising a first phase and a second phase, the first phase comprising biomolecule-saturated DME and the second phase comprising the dilute biomolecule-water solution, thereby extracting a portion of the biomolecule from the biomolecule-water solution into the DME;

b) separating the biomolecule-saturated DME phase and the biomolecule-water solution phase;

c) vaporizing the DME to vapor phase, thereby releasing the biomolecule from the DME, yielding a biomolecule-water solution of greater biomolecule concentration than the biomolecule concentration in the starting biomolecule-water solution;

d) recovering the vapor phase DME by condensing to liquid phase; and e) repeating steps a)-d), wherein the DME recovered in step d) is mixed with the dilute biomolecule-water solution in step a). In some embodiments, steps a)-d) are repeated 10 or fewer times, for example, 10, 9, 8, 7, 6, 5, 4, 3 or 2 iterations.

In a related aspect, the invention provides methods for concentrating a biomolecule, e.g., a small organic compound, e.g., one or more C2-C6 alcohols, one or more C3-C5 carboxylic acids, one or more C8-18 fatty alcohols, one or more C1-C18 dicarboxylic acids, one or more furfurals, one or more furans, one or more butanediols, one or more butadienes, and mixtures thereof from a dilute biomolecule-water solution. In some embodiments, the methods comprise:

a) mixing the dilute biomolecule-water solution with liquid phase dimethyl ether (DME), wherein the distribution coefficient for the biomolecule in a mixture of the DME and the biomolecule-water solution favors the transfer of the biomolecule from the biomolecule-water solution to the DME, thereby yielding a solution comprising a first phase and a second phase, the first phase comprising biomolecule-saturated DME and the second phase comprising the dilute biomolecule-water solution, thereby extracting a portion of the biomolecule from the biomolecule-water solution into the DME;

b) separating the first phase and the second phase; and c) converting the liquid-phase DME to vapor phase, thereby releasing the biomolecule from the DME, yielding a concentrated biomolecule-water solution.

With respect to the embodiments of the methods, in some embodiments, the methods further comprise the step of isolating the biomolecule-water solution released from the DME, e.g., when the biomolecule-water solution has a biomolecule concentration that is greater than the biomolecule concentration of the feedstock dilute biomolecule solution.

In some embodiments, steps a)-d) are repeated 10 or fewer times, for example, 10, 9, 8, 7, 6, 5, 4, 3 or 2 iterations. In various embodiments, the steps are performed as a continuous flow process. In various embodiments, the methods are performed on a large scale or a commercial scale.

For example, the methods provide an economically efficient procedure to process at least about 1 million gallons, e.g., at least about 10 million gallons, e.g., at least about 20 million gallons dilute biomolecule-water solution (e.g., fermentation broth or feedstock) annually, e.g., from about 1 million gallons to about 150 million gallons annually, e.g., from about 10 million gallons to about 100 million gallons annually, e.g., from about 20 million gallons to about 100 million gallons annually.

In some embodiments, the mixing of step a) is performed in one or more countercurrent extraction stages, for example, in 2, 3, 4, 5, 6, 7, 8, 9, 10 or more countercurrent extraction stages.

In some embodiments, the DME is recovered by vapor recompression. In some embodiments, the methods further comprise the step of condensing and reusing the vaporized DME.

In some embodiments, the vaporizing and the condensing of the DME is driven by a refrigerant circuit. In some embodiments, the refrigerant in the refrigerant circuit is selected from the group consisting of R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R 227ea, R 236ea, R 245ca, R-365mfc, RC318, R 406a, R-410a, R-414a, R-500, R-502, R-503, R-1301 and ammonia. In some embodiments, the refrigerant in the refrigerant circuit is R-134a.

In various embodiments, the unconcentrated or feedstock dilute biomolecule-water solution comprises from about 0.1 wt. % to about 10.0 wt. % biomolecule, for example, from about 0.1 wt. % to about 5.0 wt. % biomolecule, for example, from about 0.1 wt. % to about 3.0 wt. % biomolecule, for example, at least about 0.1 wt. % biomolecule and less than about 0.2 wt. %, 0.3 wt. %, 0.4 wt. %, 0.5 wt. %, 0.6 wt. %, 0.7 wt. %, 0.8 wt. %, 0.9 wt. %, 1.0 wt. %, 1.5 wt. %, 2.0 wt. %, 2.5 wt. %, 3.0 wt. %, 3.5 wt. %, 4.0 wt. %, 4.5 wt. %, 5.0 wt. %, 5.5 wt. %, 6.0 wt. %, 6.5 wt. %, 7.0 wt. %, 8.0 wt. %, 9.0 wt. % or 10.0 wt. % biomolecule. In some embodiments, the unconcentrated or feedstock dilute biomolecule-water solution is a fermentation beer or fermentation broth. In various embodiments, the unconcentrated or feedstock dilute biomolecule-water solution comprises from 2-4 wt. % ethanol. In various embodiments, the unconcentrated or feedstock dilute biomolecule-water solution comprises about 1-2 wt. % butanol (BuOH). In some embodiments, the unconcentrated or feedstock dilute biomolecule-water solution is a *Clostridium* fermentation broth. In various embodiments, the feedstock dilute biomolecule-water solution comprises cellular biomass in suspension.

In various embodiments, the concentration of the concentrated biomolecule-water solution is at least about 2-fold, 2.5-fold, 3-fold, 3.5-fold, 4-fold, 4.5-fold, 5-fold, 10-fold, 15-fold, or more, in comparison to or over the concentration of the biomolecule in the unconcentrated or feedstock dilute biomolecule-water solution. In some embodiments, the concentration of the concentrated biomolecule-water solution is at least about 7.0 wt. %, for example, at least about 8.0 wt. %, 9.0 wt. %, 10.0 wt. %, 15.0 wt. %, 20.0 wt. %, 25.0 wt. %, 30.0 wt. % biomolecule.

Generally, concentration using DME does not comprise distillation. In various embodiments, the biomolecule is further concentrated, e.g., by distillation, once the concentration of the biomolecule released from the DME is greater than a threshold or target biomolecule concentration, e.g., greater than about 7 wt. %, for example, greater than about 8.0 wt. %, 9.0 wt. % or 10.0 wt. %.

In various embodiments, the method is performed a temperature in the range of about 20° C. to about 150° C., for example, in the range of about 20° C. to about 100° C., for example in the range of about 20° C. to about 50° C. In some embodiments, the method is performed at ambient temperature, e.g., in the range of about 20° C. to about 35° C. In some embodiments, the method is performed at fermentation temperature. For example, for certain organisms, fermentation temperature is in the range of about 35° C. to about 40° C., e.g., about 35° C., 36° C., 37° C., 38° C., 39° C. or 40° C.

In various embodiments, the method is performed at a pressure in the range of about 3 bar to about 50 bar, for example, in the range of about 3 bar to about 10 bar, for example, in the range of about 5 bar to about 10 bar, for example, about 3 bar, 4 bar, 5 bar, 6 bar, 7 bar, 8 bar, 9 bar or 10 bar.

In some embodiments, the DME is mixed with the feedstock the unconcentrated or feedstock dilute biomolecule-water solution at a solvent-to-feedstock ratio in the range of about 0.5 to about 2.0, for example, from about 1.0 to about 1.5, for example, at a solvent-to-feedstock ratio of about 0.5, 0.75, 1.0, 1.25, 1.5, 1.75, or 2.0.

In some embodiments, the energy input for biomolecule concentration is less than 3000 BTU/Lb biomolecule recovered, for example, less than 2900 BTU/Lb, 2800 BTU/Lb, 2700 BTU/Lb, 2600 BTU/Lb, 2500 BTU/Lb, 2400 BTU/Lb, 2300 BTU/Lb, 2200 BTU/Lb, 2100 BTU/Lb, 2000 BTU/Lb, 1900 BTU/Lb, 1800 BTU/Lb, 1700 BTU/Lb, 1600 BTU/Lb, 1500 BTU/Lb, 1400 BTU/Lb, 1300 BTU/Lb, 1200 BTU/Lb, 1100 BTU/Lb, 1000 BTU/Lb biomolecule recovered.

In various embodiments, at least about 60%, for example, at least about 70%, 75%, 80%, 85%, 90%, 95%, or more, of the biomolecule in the feedstock dilute aqueous solution is concentrated and recovered.

In various embodiments, the biomolecule is a C2-C6 alcohol. In various embodiments, the C2-C6 alcohol is selected from ethanol, a propanol, a butanol, a pentanol and a hexanol. In some embodiments, the alcohol is a C2-C5 alcohol. In some embodiments, the alcohol is ethanol.

In some embodiments, the alcohol is a propanol or C3 alcohol. In some embodiments, the propanol is selected from the group consisting of 1-propanol and 2-propanol.

In some embodiments, the alcohol is a butanol or C4 alcohol. In some embodiments, the butanol is selected from the group consisting of 1-butanol, 2-butanol, tert-butanol (2-methyl-2-propanol), and iso-butanol (2-methyl-1-propanol).

In some embodiments, the alcohol is a pentanol or C5 alcohol. In some embodiments, the pentanol is selected from the group consisting of 1-pentanol, 2-pentanol, 3-pentanol, 2-methyl-1-butanol, 3-methyl-1-butanol, 2-methyl-2-butanol, 3-methyl-2-butanol, and 2,2-dimethyl-1-propanol.

In some embodiments, the alcohol is a hexanol or C6 alcohol. In some embodiments, the hexanol is selected from the group consisting of 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 3,3-dimethyl-1-butanol, 2,2-dimethyl-1-butanol, 2,3-dimethyl-1-butanol, 2,3-dimethyl-2-butanol, 3,3-dimethyl-2-butanol, and 2-ethyl-1-butanol.

In some embodiments, the biomolecule is a C3-C5 carboxylic acid or dicarboxylic acid, e.g., propionic acid, lactic acid, malonic acid, fumaric acid, succinic acid, itaconic acid, levulinic acid and/or 3-hydroxybutyric acid.

In some embodiments, the biomolecule is a butanediol, e.g., 1,4-butanediol and/or 2,3-butanediol.

In some embodiments, the biomolecule is a furfural, e.g., furfural (furan-2 carbaldehyde) and/or hydroxymethylfurfural (5-(hydroxymethyl)-2-furalaldehyde or HMF).

In some embodiments, the biomolecule is a C1-C18 dicarboxylic acid (e.g., a C1-C18 diacid). Illustrative C1-C18 dicarboxylic acids that can be extracted from dilute aqueous solutions using DME include without limitation propanedioic, butanedioic, pentanedioic, hexanedioic, heptanedioic, octanedioic, nonanedioic, decanedioic, undecanedioic, and dodecanedioic (DDDA).

In some embodiments, the biomolecule is a C8-C18 fatty alcohol. Illustrative C8-C18 fatty alcohols that can be extracted from dilute aqueous solutions using DME include without limitation capryl alcohol (1-octanol), 2-ethyl hexanol, pelargonic alcohol (1-nonanol), capric alcohol (1-decanol, decyl alcohol), undecyl alcohol (1-undecanol, undecanol, hendecanol), lauryl alcohol (dodecanol, 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), palmitoleyl alcohol (cis-9-hexadecen-1-ol), heptadecyl alcohol (1-n-heptadecanol, heptadecanol) and stearyl alcohol (1-octadecanol).

In some embodiments, the biomolecule is a butadiene, e.g., butadiene and/or 2-methyl-1,3-butadiene (isoprene).

In some embodiments, the biomolecule is acetoin and/or furan. Mixtures of any of the biomolecules listed above and herein can be extracted from aqueous solution using DME. In varying embodiments, the biomolecule is a mixture of acetone, butanol and ethanol (ABE). Generally, biomolecules having a solubility in water of greater than about 15 wt. % at 25° C. are substantially not extracted. In some embodiments, carbohydrates, amino acids and nucleic acids (e.g., which are water soluble) are substantially not extracted. In some embodiments, glucose and/or acetate are substantially not extracted.

In various embodiments, the biomolecule has a solubility in water of less than about 15 wt. % at 25° C., e.g., less than about 14%, 13%, 12%, 11% or 10% at 25° C. In some embodiments, the biomolecule has a carbon atom to hydroxyl group ratio of 3 or greater, e.g., a ratio of 4, 5 or 6 carbon atoms to hydroxyl groups. In some embodiments, the biomolecule has a melting point of 100° C. or less, e.g., 95° C., 90° C., 85° C., 80° C., 75° C., or less.

In various embodiments, the unextracted alcohol and residual DME in the second phase is returned to the feedstock dilute aqueous solution, e.g., wherein the feedstock dilute aqueous solution is a fermentation broth. In some embodiments, the fermentation beer or fermentation broth comprises up to about 3 wt. % DME (i.e., about 3 wt. % DME or less), e.g., about 0.5 wt. %, about 0.6 wt. %, about 0.7 wt. %, about 0.8 wt. %, about 0.9 wt. %, about 1.0 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2.0 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, or less DME.

In various embodiments, the DME, or analogs thereof, is not a polyoxaalkane, a glycol or a glyme.

DEFINITIONS

The term "alcohol component" refers to a straight or branched, saturated, radical having 2-6 carbon atoms and one or more hydroxy groups. The alkyl portion of the alcohol component can be ethyl, methyl, dimethyl, propyl, butyl, pentyl, iso-propyl, iso-butyl, sec-butyl, tert-butyl, etc. Alcohol components useful in the present invention include, but are not limited to, ethanol, propanol, isopropanol, butanol, isobutanol, t-butanol and pentanol, among others. One of skill in the art will appreciate that other alcohol components are useful in the present invention.

The terms "extraction," "extracting" and "extracted" interchangeably refer to the process of drawing one component of a mixture into another mixture. In the present invention, the biomolecule of the biomolecule-water solution is first drawn from the biomolecule-water solution into the dimethyl ether ("DME").

The phrase "converting to vapor phase" refers to the step of altering the temperature and pressure of the DME to change the phase of the DME from liquid phase or near supercritical phase to the vapor phase.

The term "liquid phase" refers to DME under the appropriate temperature and pressure conditions in order to form a liquid phase. Provided the temperature and pressure are below the critical point for DME (127.15° C. and 53.405 bar), the liquid phase of DME can be achieved through pressure alone, temperature alone, or through a combination of temperature and pressure. One of skill in the art will know what temperature and pressure are appropriate to form the liquid phase of DME.

The term "supercritical phase" refers to DME under the appropriate temperature and pressure conditions in order to form a supercritical phase or near supercritical phase. This exists at a temperature and pressure that exceeds the critical temperature of 127.15° C. and critical pressure of 54.405 bar. One of skill in the art will know what temperature and pressure are appropriate to form the supercritical phase of DME.

The term "subcritical phase" refers to a compound that is maintained at a temperature and/or pressure that is below its critical temperature and/or pressure. A compound maintained in subcritical phase can be in either gas phase or liquid phase, or both (e.g., a dense gas). The critical point of DME is 127° C. and 774.5 psi (53.4 bar; 52.7 atm). In some embodiments, the DME is maintained at a pressure well below its critical pressure, e.g., at a pressure of about 145 psi (10 bar; 9.87 atm) or less.

The term "recycle" refers to the processing of materials so that the materials can be used again. Following extraction of the alcohol and vaporization, the DME is condensed back to the liquid phase and returned to the step of alcohol extraction with DME. The recycling prevents resources from being wasted, reduces the consumption of raw materials and reduces energy usage.

The term "reuse" refers to the act of using for a subsequent time, an item that has already been used. In the present invention, the DME used in the extraction is converted to the vapor phase in order to separate the alcohol. The vapor phase DME is recycled via condensation and supplied back to the extraction apparatus, thus being used again to extract additional alcohol from the first solvent.

The term "countercurrent column" refers to a column in which liquid-liquid separation occurs using countercurrent techniques. One of skill in the art will appreciate the countercurrent techniques are useful in the methods of the present invention.

The term "distribution coefficient" refers to the ratio of concentrations of all forms of a compound (ionized and unionized) in the two phases of a mixture of two immiscible solvents at equilibrium. See, Leo, et al., Chem Rev (1971) 71(6):525-616. The distribution coefficient can be used as a measure of how hydrophilic or hydrophobic a chemical substance is. The distribution coefficient describes the pH-dependent hydrophobicity of compounds, and is related to P (the partition coefficient), which describes the hydrophobicity of neutral (i.e., unionized) compounds only. The distribution coefficient can be symbolized as "K" or "D." D (or K) is the ratio of the sum of concentrations of the solute's (e.g., alcohol) various forms in one solvent, to the sum of the concentrations of the solute's forms in the other solvent, where the units of the concentration can be weight percent, mole percent, or g/mL, and can be calculated by the following equation:

$$D_{organic/water} = [solute]_{organic}/[solute]_{water}$$

The distribution coefficient can be measured using any method known in the art. Exemplified methods include (i) the shake flask or tube method and (ii) high performance liquid chromatography (HPLC) or gas chromatography (GC). In the shake flask method, the solute in question is diluted or dissolved to equilibrium in equal volumes of a mixture of organic phase solvent and water phase solvent, then the concentration of the solute in each solvent is measured, for example, by HPLC, GC, UV/VIS spectroscopy. In HPLC, the D of a solute can be determined by correlating its retention time with similar compounds with known D values.

The term "separation factor" refers to a measure of the fold-difference or ratio of two different distribution coefficients in self-consistent units. A separation factor can be symbolized as "α" and is calculated by dividing one distribution ratio by another. The separation factor is a measure of the ability of a system to separate two solutes.

The phrase "continuous flow process" refers to a process having constant input and output. For example, when a fermentation is not rendered toxic by the solvent, the fermentation will continuously produce alcohol, which can be siphoned into an extraction process. The siphoning off of alcohol maintains a low concentration of alcohol allowing fermentation to continue indefinitely. A continuous flow process is in contrast to a process that requires batch or discontinuous processing.

A "dilute" aqueous solution as used herein means a solution containing the biomolecule, e.g., small organic compound, e.g., one or more C2-C6 alcohols, one or more C3-C5 carboxylic acids, one or more C8-18 fatty alcohols, one or more C1-C18 dicarboxylic acids, one or more furfurals, one or more furans, one or more butanediols, one or more butadienes, and mixtures thereof, at a concentration below the solubility limit of the biomolecule in the solution. Concentration can be expressed in a variety of different units, e.g. weight or volume percent, molar concentration, molal concentration or biomolecule/water w/w of v/v ratio. Unless specified otherwise, however, the concentrations are presented here as weight percent. In some embodiments, the phrase "dilute biomolecule-water solution" refers to a solution comprising water and about 10 wt. % or less of one or more biomolecules, for example, in the range of about 0.1 wt. % to about 10 wt. %, for example, about 10%, 9%, 8%, 7%, 6%, 5%, 4%, 3%, 2%, 1%, 0.8%, 0.5%, 0.3%, 0.2% or 0.1% wt. %, or less, of biomolecule.

The term "fermentation" or "fermentation process" is defined as a process in which a biocatalyst is cultivated in a culture medium containing raw materials, such as feedstock and nutrients, wherein the biocatalyst converts raw materials, such as a feedstock, into products. The biocatalyst may be any microorganism, e.g., a yeast or bacterium, capable of converting a selected feedstock to a desired biomolecule (e.g., a C2-C6 alcohol). Any feedstock that contains a fermentable carbon source is suitable for the present invention.

The terms fermentation broth and fermentation medium are synonymous. Unless explicitly noted, the term fermentation broth should be construed to include both fermentation broth containing micro-organisms as well as fermentation broth which does not contain microorganisms.

A "solution of greater biomolecule concentration" refers to a solution of biomolecule that has been subjected to an extraction process of the invention with a detectably greater concentration of biomolecule in comparison to the feedstock solution of biomolecule. Determination of biomolecule concentrations in a biomolecule solution (e.g., a biomolecule-water solution) are well known in the art. Biomolecule concentrations can be determined using any method known in the art, including for example, gas chromatography or Karl-Fischer titration analysis. The amount of change in concentration will typically depend on the concentration of biomolecule in the feedstock solution. Extraction of a feedstock biomolecule-water solution of low biomolecule concentration will result in an end product with a relatively larger amount of biomolecule concentration. Known assays can detect biomolecule concentration changes of at least about 0.1%. Using the extraction methods of the invention, the end product solution can have a biomolecule concentration that is at least about 5%, 10%, 20%, 30%, 50%, 1-fold, 2-fold, 2.5-fold, 3-fold, 3.5-fold, 4-fold, 4.5-fold, or more, greater than the feedstock biomolecule-water solution.

The phrase "fluid communication" refers to at least two elements that are connected in such a way to allow for the free flow of a fluid medium from the one element to the second element. Two elements can optionally be connected by a controller (e.g., a valve) of the flow of the fluid medium.

The term "consisting essentially of" refers to the extractants expressly identified (i.e., DME) and excludes extractants not expressly identified (e.g., organic solvents).

In the context of performance of method steps, the term "directly" refers to sequentially performed steps excluding intermediary actions not expressly identified. In various embodiments, the methods do not comprise distillation and/or freezing.

DETAILED DESCRIPTION

1. Introduction

Figure 1:
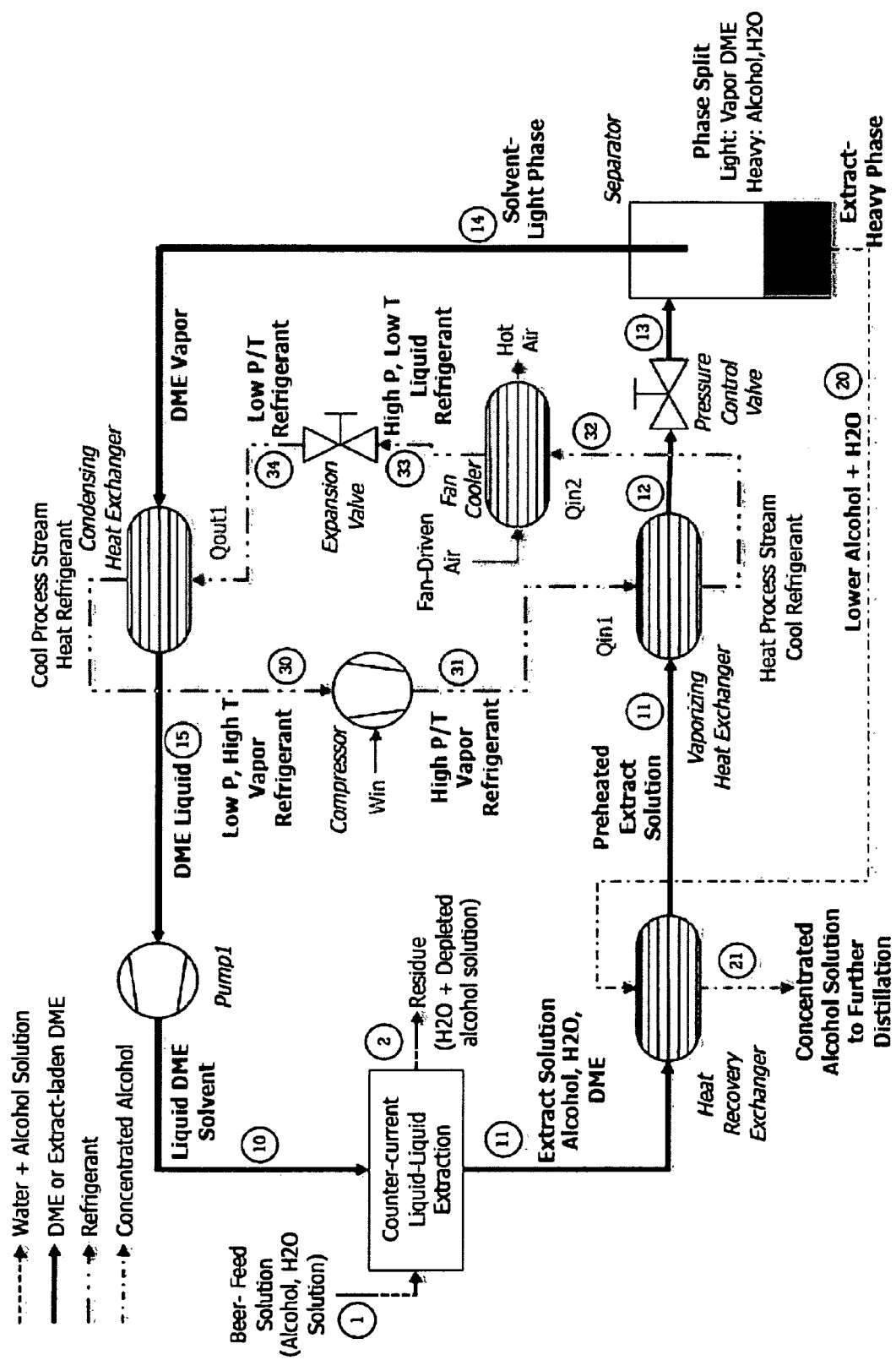
FIG. 1 illustrates a schematic for continuous flow, energy efficient concentration of lower alcohols from aqueous solution using DME liquid-liquid-extraction.

The present invention is based, in part, on the discovery that liquid phase dimethyl ether ("DME") can be used as a solvent to efficiently concentrate low concentrations of biomolecules, e.g., small organic compounds, e.g., one or more C2-C6 alcohols, one or more C3-C5 carboxylic acids, one or more C8-18 fatty alcohols, one or more C1-C18 dicarboxylic acids, one or more furfurals, one or more furans, one or more butanediols, one or more butadienes, and mixtures thereof, from aqueous solutions. Concentration of dilute concentrations of biomolecules, including lower alcohols, is achieved by contacting the dilute aqueous solution with a sufficient amount of liquid phase dimethyl ether, which has the characteristics of a favorable distribution coefficient for biomolecules, e.g., one or more C2-C6 alcohols, one or more C3-C5 carboxylic acids, one or more C8-18 fatty alcohols, one or more C1-C18 dicarboxylic acids, one or more furfurals, one or more furans, one or more butanediols, one or more butadienes, and mixtures thereof, between the aqueous solution and the DME solvent and is non-toxic to a fermentation bath. When combined with a biomolecule-water solution, the DME dissolves a portion of the biomolecule present and a more limited portion of the water present, producing a biphasic solution comprising a first phase enriched with DME and biomolecule and a second water-rich phase. The DME-biomolecule rich phase is separated from the water-rich phase. The pressure and temperature are then adjusted so that the DME can be converted to the vapor phase and the liquid alcohol in the first can be recovered and/or subject for further concentration. This invention provides a means to more energy efficiently separate the dilute biomolecules from water (as is typical of a fermentation bath). The methods of the invention can extract biomolecules from an aqueous solution in an energetically and economically favorable manner and without the need for distillation of the biomolecules from water.

In preferred embodiments, the methods are performed as a continuous flow process, wherein materials are continuously flowing from one step to the next, or from one element to the next in the present systems. In some embodiments, materials (e.g., the DME as extraction solvent) are recycled and reused. The recycling and reuse of materials provides several energy savings. Additional energy savings derive from the lack of a distillation step or a freezing step in the in the concentration of dilute amounts of biomolecule in the aqueous solution. Instead of an energy inefficient process requiring distillation of dilute concentrations of biomolecules from water, the present invention uses liquid phase DME to extract the biomolecule. The DME containing the biomolecule is then vaporized to separate from the biomolecule, followed by condensation of the DME in order to recycle and reuse the DME. The total energy required to achieve the biomolecule separation from water is much less than that required by conventional distillation and dehydration via molecular sieve. Accordingly, the methods of the present invention provide an energy efficient process for extracting biomolecules from a dilute biomolecule-water solution. Moreover, the methods provide an economically efficient procedure to process large scale volumes of biomolecules from a dilute biomolecule-water solution, e.g., at least about 1 million gallons, at least about 10 million, at least about 20 million gallons dilute biomolecule-water solution annually.

The methods find use for cellulosic ethanol production. At an ethanol ("EtOH") concentration of approximately 7 wt. %, distillation becomes energetically and economically practical. Unfortunately, given the current state of the art in cellulosic ethanol production, it is difficult to convert cellulose to sugar in sufficient quantity to create a beer (dilute ethanol broth) solution greater than 4 wt. %. Using DME as a concentrating extraction solvent enables cellulosic ethanol production to proceed with presently existing enzymes and technology without requiring increases in enzymatic efficiency or increases in the solids loading in water. The current art supports solids loading in the range of about 12 wt. % with a conversion efficiency of about 60%. The amount of alcohol is about half this amount or 3.6 wt. % EtOH (12 wt. % solids×60% conversion efficiency to sugar×50% conversion to EtOH from sugar).

2. Methods for Extracting Biomolecules from Dilute Aqueous Solution a. Feedstock The methods involve mixing a biomolecule-water solution with liquid phase DME. The biomolecule-water solution can be any aqueous solution comprising one or more biomolecules, e.g., small organic compounds, e.g., one or more C2-C6 alcohols, one or more C3-C5 carboxylic acids, one or more C8-18 fatty alcohols, one or more C1-C18 dicarboxylic acids, one or more furfurals, one or more furans, one or more butanediols, one or more butadienes, acetoin, furan, and mixtures thereof.

Generally, biomolecules suitable for extraction from dilute aqueous solutions using DME are small organic compounds. Generally, biomolecules having a solubility in water of greater than about 15 wt. % at 25° C. are substantially not extracted (e.g., not extracted in measurable or significant levels). In some embodiments, carbohydrates, amino acids and nucleic acids are substantially not extracted or not extracted. In some embodiments, glucose and/or acetate are substantially not extracted.

Generally, biomolecules suitable for extraction from a dilute aqueous solution using DME are small organic compounds with the following functional attributes or characteristics:

Exhibit low hydrogen bonding and have low solubility in water, on the order of less than about 15 wt. % solubility in water at an ambient temperature of 25° C.

Have a relatively high carbon atom number to hydroxyl group ratio, for example a ratio of 3 or greater. The higher the carbon atom number to hydroxyl group ratio, the higher the viability for the extraction from water with DME. For example, methanol would have a poor DC from water with DME, yet butanol has a very favorable DC from water with DME.

Have a relatively low melting point, e.g., a melting point of less than about 100° C. The higher the melting point of a compound the higher the level of crystallinity. Highly crystalline solids can be difficult to dissolve in any organic solvent; compounds with very high melting points are expected to exhibit low solubility in DME.

Illustrative lower alcohols include ethanol, a propanol (i.e., a C3 alcohol), a butanol (i.e., a C4 alcohol) and a pentanol (i.e., a C5 alcohol). In some embodiments, the alcohol is ethanol. In some embodiments, the alcohol is a propanol, e.g., 1-propanol or 2-propanol. In some embodiments, the alcohol is a butanol, e.g., 1-butanol, 2-butanol, tert-butanol (2-methyl-2-propanol), or iso-butanol (2-methyl-1-propanol). In some embodiments, the alcohol is a pentanol, e.g., 1-pentanol, 2-pentanol, 3-pentanol, 2-methyl-1-butanol, 3-methyl-1-butanol, 2-methyl-2-butanol, 3-methyl-2-butanol, or 2,2-dimethyl-1-propanol. In some embodiments, the alcohol is a hexanol, e.g., 1-hexanol, 2-hexanol, 3-hexanol, 2 methyl-1-pentanol, 3-methyl-1-pentanol, 4-methyl-1-pentanol, 2-methyl-2-pentanol, 3 methyl-2-pentanol, 4-methyl-2-pentanol, 2-methyl-3-pentanol, 3-methyl-3-pentanol, 3,3 dimethyl-1-butanol, 2,2-dimethyl-1-butanol, 2,3-dimethyl-1-butanol, 2,3-dimethyl-2-butanol, 3,3-dimethyl-2-butanol, and 2-ethyl-1-butanol.

Illustrative C3-C5 carboxylic acids and dicarboxylic acids include without limitation, e.g., propionic acid, lactic acid, malonic acid, fumaric acid, succinic acid, itaconic acid, levulinic acid and 3-hydroxybutyric acid. Illustrative C1-C18 dicarboxylic acids that can be extracted from dilute aqueous solutions using DME include without limitation propanedioic, butanedioic, pentanedioic, hexanedioic, heptanedioic, octanedioic, nonanedioic, decanedioic, undecanedioic, and dodecanedioic (DDDA).

Illustrative C8-C18 fatty alcohols that can be extracted from dilute aqueous solutions using DME include without limitation capryl alcohol (1-octanol), 2-ethyl hexanol, pelargonic alcohol (1-nonanol), capric alcohol (1-decanol, decyl alcohol), undecyl alcohol (1-undecanol, undecanol, hendecanol), lauryl alcohol (dodecanol, 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), palmitoleyl alcohol (cis-9-hexadecen-1-ol), heptadecyl alcohol (1-n-heptadecanol, heptadecanol) and stearyl alcohol (1-octadecanol).

In some embodiments, the biomolecule is a butanediols include, e.g., 1,4-butanediol and/or 2,3-butanediol. Illustrative furfurals include, e.g., furfural (furan-2 carbaldehyde) and/or hydroxymethylfurfural (5-(hydroxymethyl)-2-furalaldehyde or HMF). Illustrative butadienes include, e.g., butadiene and/or 2-methyl-1,3-butadiene (isoprene). In some embodiments, the biomolecule is acetoin and/or furan. Mixtures of any of the biomolecules listed above and herein can be extracted from an aqueous solution using DME.

In some embodiments, the biomolecule-water solution is a dilute biomolecule solution comprising about 10 wt. % or less of the biomolecule, for example less than about 10%, 9%, 8%, 7%, 6%, 5%, 4%, 3%, 2%, 1%, 0.9%, 0.8%, 0.7%, 0.6%, 0.5%, 0.4%, 0.3% or 0.2% biomolecule and more than about 0.1% biomolecule. In some embodiments, the biomolecule-water solution has been subjected to at least one iteration of concentration and is being subject to subsequent iterations of concentration.

In various embodiments, the biomolecule-water solution can be from fresh or unconcentrated feedstock, for example, from a fermentation broth. Any feedstock that contains a fermentable carbon source is suitable for embodiments of the present invention that include a step of culturing a microorganism. Examples include feedstocks containing polysaccharides, such as starch, cellulose and hemicellulose, feedstocks containing disaccharides, such as sucrose, sugarcane juice and sucrose-containing molasses, and monosaccharides, such as glucose and fructose. Suitable feedstocks include starchy crops, such as corn and wheat, sugarcane and sugar beet, molasses and lignocellulosic material. Suitable feedstocks also include algae and microalgae. Where desired, the feedstock may undergo treatments such as comminution, milling, separation of the carbon source from other components, such as proteins, decrystallization, gelatinization, liquefaction, saccharification, and hydrolysis catalyzed by means of chemical and/or enzymatic catalysts. Such treatment can be conducted prior to fermenting or simultaneously with it, e.g. as in simultaneous saccharification and fermentation. In various embodiments, the feedstock biomolecule-water solution can be a fermentation broth or beer, e.g., from the fermentation of fruits, amylaceous grains and tubers (e.g., corn and potatoes), cane sugar, grasses and/or cellulose.

Suitable microorganisms can be selected from naturally occurring microorganisms, genetically engineered microorganisms and microorganisms developed by classical techniques, or a combination thereof. Such microorganisms can include, without limitation, bacteria and fungi (including yeast). For example, suitable bacteria can include those that are capable of biomolecule production (e.g., lower alcohols, carboxylic acids, dicarboxylic acids, butadiene, butanediols, furfural) such as the bacteria of the *Clostridium* species. Examples of these include without limitation, *Clostridium butyricum, Clostridium acetobutylicum, Clostridium saccharoperbutylacetonicum, Clostridium saccharobutylicum* and *Clostridium beijerickii*.

Suitable bacteria and fungi also include those that are capable of hydrolyzing carbohydrates and can be genetically engineered to produce alcohols and/or other biomolecules suitable for extraction from an aqueous solution using DME. Illustrative species include, without limitation, bacteria of the order *Clostridiales* (e.g. *Butyrovibrio fibrisolvens*), *Bacilliales* (e.g. *Bacillus circulans*), *Actinomycetales* (e.g. *Streptomyces cellulolyticus*), *Fibrobacterales* (e.g. *Fibrobacter succinogenes*), *Xanthomonadales* (*Xanthomonas* species) and *Pseudomonadales* (e.g. *Pseudomonas mendocina*) and fungi such as those of the order *Rhizopus, Saccharomycopsis, Aspergillus, Pichia, Schwanniomyces* and *Polysporus*. The fungi may be able to do the conversion aerobically or anaerobically. Examples of anaerobic fungi include, without limitation, *Piromyces* species (e.g. strain E2), *Orpinomyces* species (e.g. *Orpinomyces bovis*), *Neocallimastix* species (*N. frontalis*), *Caecomyce* species, *Anaeromyces* species and *Ruminomyces* species.

As noted above, any microorganism, whether naturally occurring or manmade, that is capable of producing alcohol and/or other biomolecules suitable for extraction from an aqueous solution using DME can be used and the methods of the present invention are not limited to the examples listed here. In some embodiments, the microorganism is viable at temperatures from about 20° C. to about 95° C. Reference to a microorganism being viable at a given temperature or range of temperatures refers to a microorganism being able to survive exposure to such temperatures and subsequently be able to grow and/or produce metabolic products under the same or different conditions. In other embodiments, the microorganism is a temperature resistant microorganism. In other embodiments, the microorganism is a DME resistant microorganism. The term "resistance" is defined as the property of a biocatalyst to have a low rate of inhibition in the presence of increasing concentrations of an inhibitor in the fermentation broth.

The term "tolerance" is defined as the ability of the biocatalyst to maintain its specific productivity at a given concentration of an inhibitor. The term "tolerant" describes a biocatalyst that maintains its specific productivity at a given concentration of an inhibitor. For example, if in the presence of 2% of an inhibitor a biocatalyst maintains the specific productivity that it had at 0 to 2%, the biocatalyst is tolerant to 2% of the inhibitor or has a tolerance to 2% of the inhibitor. The term "tolerance to temperature" is defined as the ability of the biocatalyst to maintain its specific productivity at a given temperature. The term "tolerance to DME" is defined as the ability of the biocatalyst to maintain its specific productivity at a given concentration of DME.

In some embodiments, the microorganism has a productivity of at least about 0.5 g/L per hour of the C3-C6 alcohol in aggregate over the lifetime of a batch fermentation cycle. In some embodiments, the productivity is at least about 1, at least about 1.5, at least about 2.0, at least about 2.5, at least about 3, at least about 3.5, at least about 4.0, at least about 4.5, and at least about 5.0 g/L per hour of the C3-C6 alcohol in aggregate over the lifetime of a batch fermentation cycle. In some embodiments, the productivity ranges from about 0.5 g/L per hour to about 5 g/L per hour of the C3-C6 alcohol over the lifetime of a batch fermentation cycle.

In some embodiments, the feedstock is an acetone-butanol-ethanol (ABE) fermentation broth or beer, e.g., resulting from bacterial fermentation to produce acetone, n-butanol and ethanol from starch. Such ABE solutions are produced by bacteria of the genus *Clostridium*, including *Clostridium acetobutylicum, Clostridium beijerinckii, Clostridium butyricum*, and *Clostridium saccharoperbutylacetonicum*. ABE solutions generally comprise acetone, n-butanol and ethanol in a ratio of about 3-6-1 (i.e., 3 parts acetone, 6 parts butanol and 1 part ethanol), and in dilute concentrations (about 0.2 wt. % acetone, about 0.6 wt. % n-butanol, and about 0.1% ethanol).

Preferably, the feedstock is an aqueous solution where the biomass has been substantially removed. Usually, the feedstock is an aqueous solution where solids have been substantially removed.

b. Contacting Feedstock with Dimethyl Ether

The solution comprising dilute concentrations of a lower alcohol and/or other biomolecules suitable for extraction from an aqueous solution using DME is contacted with dimethyl ether (DME) under conditions sufficient to concentrate the biomolecule(s) of interest (e.g., lower alcohols, carboxylic acids, dicarboxylic acids, butadiene, butanediols, furfural) into the DME.

In some embodiments, the biomolecule-water solution is contacted with DME that is in subcritical phase, i.e., at a temperature and pressure that is below the critical temperature and pressure for DME. In various embodiments of performing the present methods, the DME can be delivered and maintained at ambient temperature and at a pressure that is well below its critical pressure of about 774.5 psi (53.4 bar; 52.7 atm).

In various embodiments, the methods are performed at a temperature in the range of about 20° C. to about 35° C., for example, about 20° C., 21° C., 22° C., 23° C., 24° C., 25° C., 26° C., 27° C., 28° C., 29° C., 30° C., 31° C., 32° C., 33° C., 34° C. or 35° C. In various embodiments, the methods are performed at a fermentation temperature. For example, for certain organisms, fermentation temperature is in the range of about 35° C. to about 40° C., for example at a temperature of about 35° C., 36° C., 37° C., 38° C., 39° C. or 40° C.

In some embodiments, the DME is delivered and maintained in liquid phase. For example, the DME is delivered and maintained at a pressure at or above the vapor pressure, e.g., above about 85 psi (5.9 bar; 5.8 atm) and below 145 psi (10 bar; 9.87 atm), for example, about 85 psi (5.9 bar; 5.8 atm); 87 psi (6 bar; 5.9 atm); 102 psi (7 bar; 6.9 atm); 116 psi (8 bar; 7.9 atm); 131 psi (9 bar; 8.9 atm); or 145 psi (10 bar; 9.87 atm). In performing the present methods, the DME can be delivered and maintained at ambient temperature and at a pressure that above the vapor pressure and below its critical pressure of about 774.5 psi (53.4 bar; 52.7 atm).

The DME can be added in an amount such that the DME ratio with the dilute aqueous solution feedstock (i.e., solvent-to-feed ratio) is about 2:1 to about 1:1, for example, about 1.5:1 to about 1:1, for example about 2.0:1, 1.9:1, 1.8:1, 1.7:1, 1.6:1, 1.5:1, 1.4:1, 1.3:1, 1.2:1, 1.1:1 or 1.0:1.

The DME can be contacted and mixed with the aqueous solution comprising dilute concentrations of the biomolecule(s) of interest using any method known in the art. Those of skill will appreciate that the delivery method will be appropriate to the phase of the DME solvent, e.g., liquid, subcritical, or supercritical phase. The DME can be delivered in continuous or batch processing, with sufficient agitation to mix homogeneously with the aqueous solution. In some embodiments, the DME is contacted with the biomolecule-water solution in a countercurrent manner. For example, gas-phase DME can be bubbled up through a vertical column through which the aqueous solution is being poured down. In other embodiments, the DME is mixed with the aqueous solution using a mixer, e.g., an in-line mixer.

The DME can be unused or recycled from a previous extraction stage or iteration. In embodiments performing liquid-liquid extraction in a countercurrent column, the DME can be introduced into the base of the column. The column can be adjusted in length and width (e.g., internal diameter) to enable sufficient residence time contact between the aqueous solution with the rising DME in the column. In varying embodiments, the columns can be as short as 10 cm and as long as 30 m, for example, about 0.01 m, 0.05 m, 0.10 m, 0.5 m, 1.0 m, 1.5 m, 2.0 m, 2.5 m, 3.0 m, 3.5 m, 4.0 m, 4.5 m 5.0 m, 5.5 m, 6.0 m, 6.5 m, 7.0 m, 7.5 m, 8.0 m, 8.5 m, 9.0 m, 9.5 m, 10 m, 15 m, 20 m, 25 m or 30 m. In some embodiments, the column has a length in the range between 2 m and 5 m. As the DME moves up the column, it extracts the biomolecule(s) of interest from the aqueous solution. The biomolecule(s) extracted into the DME can be discharged in the column at a fluid level above the elevation of the input for the aqueous solution. In varying embodiments, the column inside diameter (ID) can be in the range of about 0.01 m to about 10 m, e.g., about 0.01 m, 0.04 m, 0.05 m, 0.08 m, 0.10 m, 0.5 m, 1 m, 1.5 m, 2 m, 2.5 m, 3 m, 3.5 m, 4 m, 4.5 m, 5 m, 6 m, 7 m, 8 m, 9 m or 10 m. In some embodiments, the ID is in the range of between about 0.04 m and about 2.0 m. In varying embodiments, the length/ID ratio is in the range of between about 5 and about 200, e.g., about 5, 10, 20, 25, 50, 75, 100, 125, 150, 175 or 200. In some embodiments, the length/ID ratio is in the range of between about 20 and about 60, e.g., about 20, 25, 30, 35, 40, 45, 50, 55 or 60. In varying embodiments, the superficial flow velocity as defined by the ratio of the total volumetric flow to the inside column area is in the range of between about 0.1 cm/sec and about 100 cm/sec, e.g., 0.1 cm/sec, 0.5 cm/sec, 1.0 cm/sec, 5 cm/sec, 10 cm/sec, 15 cm/sec, 20 cm/sec, 25 cm/sec, 50 cm/sec, 75 cm/sec, or 100 cm/sec. In some embodiments, the superficial flow velocity as defined by the ratio of the total volumetric flow to the inside column area is in the range of between about 5 to about 15 cm/sec.

Figure 10:
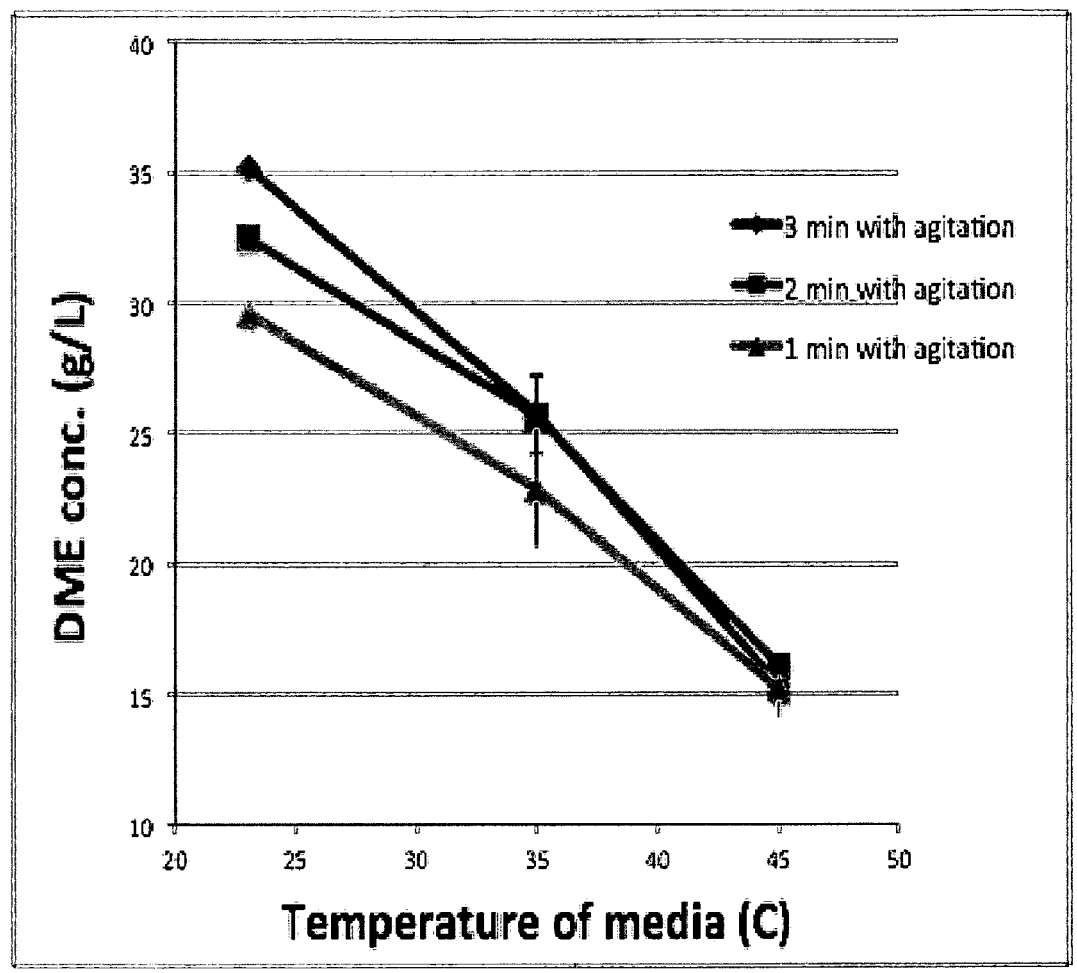
FIG. 10 illustrates DME dissolved in media at various temperatures and after various sparging/agitation times.

Methods for performing liquid-liquid extraction ("LLE") in a countercurrent column have been well documented in the literature, e.g., by Treybal, Robert E., "Liquid Extraction," McGraw-Hill, New York, 1951). Each countercurrent stage can be implemented with a mixer and settler. As an integrated system with multiple stages, a spray tower may be used (e.g., per FIG. 10.1 in Treybal). In addition, conventional tray columns using disk and donut baffles find use (FIGS. 10.4a and 10.4b in Treybal). Further, a column with random packing and flow distributor regions, using packing such as rashig rings, Pall Rings, Intalox saddles, or berl saddles, find use. In addition, a Podbielniak extractor could optionally be used (FIG. 10.12 in Treybal). Such devices are also described, e.g., in Perry's Chemical Engineering Handbook (Chapter 15, 8th edition, 2008). Columns that find use in the present extraction methods include static extraction columns, agitated extraction columns, mixer-settlers, or centrifugal extractors. Any one of these configurations can be configured to implement the desired number of stages. Economics, as constrained by throughput and equipment space constraints, would define the preferred configuration. An illustrative multistage centrifugal extractor is available from Robatel, Inc. (on the internet at rousselet-robatel.com/products/multistage-centrif-extractors-lx.php). Use of centrifugal countercurrent columns for continuous LLE is also described, e.g., on the internet at cheresources.com/centcontactor.shtml.

Extraction can be performed in one or more sequentially arranged countercurrent columns, i.e., in one or more stages. In various embodiments, the biomolecule(s) are extracted from the aqueous solution in 2, 3, 4, 5, 6, 7, 8, 9 or 10 countercurrent extraction stages (see, FIG. 2), as appropriate. In some embodiments, 5-7 countercurrent liquid-liquid extraction stages are performed, for example, 5, 6 or 7 countercurrent liquid-liquid extraction stages.

Following one or more extraction stages, the DME/biomolecule stream can then pass onto a liquid recovery step, for recycling of the DME and recovery of the concentrated biomolecule. In varying embodiments, the mass ratio of DME to aqueous solution is in the range of from about 0.5 to about 20, e.g., about 0.5, 1, 2, 3, 4, 5, 6, 7, 8, 9, 10, 11, 12, 13, 14, 15, 16, 17, 18, 19, or 20. In some embodiments, the mass ratio of DME to aqueous solution is in the range of from about 1 to about 3.

c. Separating the Biomolecule-Saturated DME Phase and the Biomolecule-Water Solution Phase After mixing DME with the dilute biomolecule-water solution, the biomolecule-saturated DME phase and the biomolecule-water solution phase (i.e., raffinate) can be separated using any method known in the art.

For example, in embodiments where the DME is mixed with the dilute biomolecule-water solution in one or more countercurrent stages of liquid-liquid extraction, the biomolecule-saturated DME phase and the biomolecule-water solution phase are separated upon exit of opposite ends of the countercurrent column.

In some embodiments, the biomolecule-saturated DME phase and the biomolecule-water solution phase naturally separate (e.g., due to a density differential) such that the phased can be physically isolated from one another, e.g., the relatively less dense biomolecule-saturated DME phase can be decanted from the relatively more dense biomolecule-water solution phase.

DME can be further removed or reduced from the biomolecule-saturated DME phase and residual DME can be removed or reduced from the biomolecule-water solution phase by vaporization. This can be accomplished using any method in the art, for example, reducing pressure or heat input (flash to vaporization).

d. Recycling/Reusing Dimethyl Ether

In various embodiments, the methods further comprise the step of recovering all or part the DME from the biomolecule and/or aqueous solution. This can be done using any method known in the art. For example, the DME/biomolecule/water solution can be passed through a heat exchanger (i.e., vaporizer) that imparts sufficient enthalpy into the stream to enable the DME to flash to vapor upon flowing through a pressure reduction valve into a separator. Following the pressure reduction valve, a DME-dominated vapor stream and a solvent-dominated liquid stream results. The DME-dominated stream can be subsequently passed through a cooling heat exchanger (i.e., condenser) to liquify the DME. This recycled DME can be fed back to the countercurrent column for additional LLE stages, as needed or desired.

The energetics of using, reusing and recycling DME are improved by driving its vaporization and condensation using a heat pump or refrigerant circuit. This is depicted in FIG. 1. In one embodiment, the refrigerant used allows the temperature range for the DME to fluctuate from about 20° C. to about 30° C., where 20° C. is the condensation temperature and 30° C. is the flash-to-vaporization temperature. To drive this temperature difference, a heat pump with conditions that go between 15° C. and 35° C. is used. Thus, there is a 5° C. temperature difference to drive both condensation and vaporization. In this temperature range, the refrigerant R-134a finds use. At 15° C., R-134a condenses 20° C. DME and at 35° C., R134a vaporizes 30° C. DME. In this particular case, the amount of energy to drive the DME loop is calculated to be 0.0095 kW/(kg/hr) or 9.5 kW/1000 kg/hr DME flow based on thermal balance and thermodynamic properties of the DME and R-134a.

Other temperature ranges/pressures will work, and other refrigerants, also find use. In some embodiments, the refrigerant used to drive the heat pump or refrigerant circuit is selected from R-11, R-12, R-13, R-14, R-21, R-22, R-23, R-41, R-113, R-114, R-115, R-116, R-123, R-124, R-125, R-134a, R-141b, R-142b, R-143a, R-152a, R-218, R-227ea, R-236ea, R-245ca, R-365mfc, RC318, R 406a, R-410a, R-414a, R-500, R-502, R-503, R-1301 and ammonia.

To provide illustrative examples, the energy expenditure of alcohol concentration from dilute aqueous solutions can be estimated from the thermodynamic properties of the alcohol solution. Energy input estimates of four test cases for the 3-fold concentration of ethanol are calculated to illustrate.

For a SF=150% (i.e., a solvent-to-feed ratio of 1.5:1) and 6 liquid-liquid-extraction ("LLE") stages, the following applies for dilute EtOH solution:

For 2 wt. % EtOH solution, the energy required is 0.903 kW-hr/kg=3249 kJ/kg=1397 BTU/lb.

For 3 wt. % EtOH solution, the energy required is 0.643 kW-hr/kg=2313 kJ/kg=995 BTU/lb For 3.5 wt. % EtOH solution, the energy required is 0.549 kW-hr/kg=1975 kJ/kg=849 BTU/lb For 4 wt. % EtOH solution, the energy required is 0.478 kW-hr/kg=1722 kJ/kg=740 BTU/lb With the addition of this energy, the concentration of the EtOH is increased by roughly a factor of 3. This means that an aqueous solution comprising about 3 wt. % EtOH is concentrated to an aqueous solution comprising about 9 wt. % EtOH; an aqueous solution comprising about 3.5 wt. % EtOH is concentrated to an aqueous solution comprising about 10.5 wt. % EtOH; and an aqueous solution comprising about 4 wt. % EtOH is concentrated to an aqueous solution comprising about 12 wt. % EtOH. This increase in concentration via DME LLE is much more energetically and economically efficient than using distillation over the same concentration ranges. Distillation energy would require between about 2 and 10 times greater energy input than the present DME extraction methods.

Concentrated EtOH can be separated or isolated and subject to further concentration, e.g., using other techniques. For example, distillation can be used to boost the ethanol content to concentrations above the higher concentration, e.g., from about 10% to approximately 90 wt. % or more, wherein at higher concentrations molecular sieves become practical for increasing the EtOH to nearly anhydrous level.

In addition, the DME LLE can be applied to concentrating butanol and/or ethanol from ABE solution. Energy input estimates of two test cases are calculated to illustrate:

For 1 wt. % BuOH solution, SF=100% (i.e., a solvent-to-feed ratio of 1:1), and 8 LLE stages, the energy required is 1.092 kW-hr/kg=3932 kJ/kg=1691 BTU/lb For 2 wt. % BuOH solution, SF=140% (i.e., a solvent-to-feed ratio of 1.4:1), and 6 LLE stages, the energy required is 0.698 kW-hr/kg=2514 kJ/kg=1081 BTU/lb In the case of butanol, DME LLE achieves an increase in concentration of approximately 4-fold. This means that an aqueous solution comprising about 1 wt. % BuOH is concentrated to an aqueous solution comprising about 4 wt. % BuOH. An aqueous solution comprising about 2 wt. % BuOH, is concentrated to an aqueous solution comprising about 8 wt. % BuOH. BuOH has a limited solubility in water of approximately 7 wt. %. This means when concentrated to about 8 wt. %, a portion of BuOH would form a second, BuOH-rich phase that can be physically decanted from the water. This forms a highly efficient approach for separating BuOH from aqueous solution.

In the process of extracting the BuOH, both acetone and ethanol would also be extracted. Subsequent distillation of the BuOH/acetone/ethanol mixture could be used to achieve pure streams; however, the amount of water would be substantially reduced. DME LLE provides for an improved energy efficiency versus conventional distillation of the dilute ABE solution or adsorption-distillation—the current benchmark process for energy efficient separation of BuOH from dilute solution. Distillation requires between 2 and 10 times more energy input than the DME LLE method.

In other embodiments, the DME is condensed using vapor recompression. Vapor recompression is simpler and is commonly used in the oil and gas industries. However, implementing vapor recompression requires a compressor of specific design for use with flammable media (i.e., DME). Use of a refrigerant circuit has the advantage that it can be implemented with commercial off-the-shelf refrigerant equipment (e.g., refrigerant compressors, expansion valves, heat exchangers).

e. Separating/Isolating Concentrated Biomolecule

DME concentration of the biomolecule from the aqueous solution can proceed in a continuous and iterative manner until a desired threshold concentration is achieved. The threshold concentration can be based on the starting concentration of biomolecule in the feedstock material, for example, the threshold concentration may be 1-fold, 2-fold, 2.5-fold, 3-fold, 3.5-fold, 4-fold, 4.5-fold, 5-fold, or greater, in comparison to the concentration of the biomolecule in the feedstock material. In various embodiments, the threshold concentration is a target concentration of biomolecule in the aqueous solution, for example, 7 wt. %, 8 wt. %, 9 wt. %, 10 wt. %, 11 wt. %, 12 wt. %, 13 wt. %, 14 wt. % or 15 wt. % biomolecule.

Once a threshold concentration level of the biomolecule is achieved, the concentrated biomolecule can be isolated. This can be done using any method known in the art. As discussed above, the biomolecule can be released from the DME by vaporizing the liquid phase DME. The biomolecule may be subject to further concentration procedures, e.g., by distillation. Depending on the composition of the starting feedstock material, the DME may co-concentrate other compounds with the biomolecule. The biomolecule can be purified or separated from such compounds, as needed or desired, using methods known in the art.

f. Illustrative Embodiments i. Concentration of Dilute Ethanol (EtOH) Aqueous Solutions One illustrative embodiment for the concentration of dilute concentrations of ethanol from an aqueous solution, e.g, a fermentation broth, is provided in FIG. 1. An aqueous solution, e.g, a fermentation broth, comprising less than about 5% ethanol (e.g., from about 0.1% to about 3% ethanol) is contacted with liquid phase DME at about a 1.5:1 solvent to feed ratio in a countercurrent column maintained at a pressure of about 8 bar and at a temperature of about 38° C. The DME is mixed with the dilute EtOH aqueous solution in sequential countercurrent columns, extracting the EtOH into the DME over 5-7 liquid-liquid extraction stages.

The aqueous phase comprising DME saturated with EtOH is delivered to a flash column and exposed to a flash temperature in the range of about 110-130° C. to remove the DME by vaporization. The vaporized DME is condensed back to liquid phase for recycling and reuse. The vaporization and condensation of DME is driven by a refrigeration circuit, e.g., using the refrigerant R134a. Residual DME remaining in the concentrated EtOH after flash vaporization can be removed by distillation. Under these parameters, it is possible achieve about 50-60% recovery and a 3-fold concentration of the EtOH from the feedstock aqueous solution with an energy input of less than about 1500 BTU/lb EtOH recovered, for example, less than about 1000 BTU/lb EtOH recovered.

DME is recovered from the aqueous phase comprising unextracted EtOH (i.e., the raffinate) by reducing pressure (e.g., to about 300 torr; 0.4 atm; 0.4 bar; 5.8 psi), thereby vaporizing the DME in the aqueous raffinate. Residual DME in the aqueous raffinate, about 6%, can be returned to the fermenter (after sterilization). Raffinate returned to the fermentation medium comprises a portion of the total fermentation medium such that the total concentration of DME in the fermentation medium is less than 3 wt. %, for example, less than about 0.5 wt. %, about 0.6 wt. %, about 0.7 wt. %, about 0.8 wt. %, about 0.9 wt. %, about 1.0 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2.0 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, or about 2.9 wt. % DME.

ii. Concentration of Dilute Butanol (BuOH) Aqueous Solutions

Figure 2:
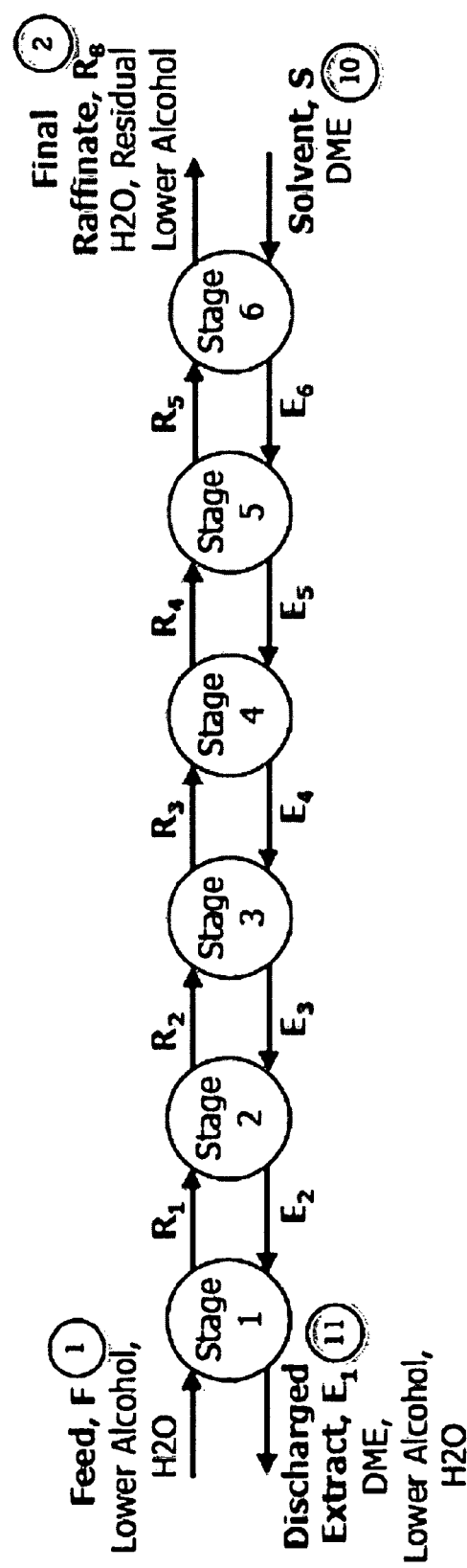
FIG. 2 illustrates a schematic for multistage countercurrent LLE.
Figure 2:
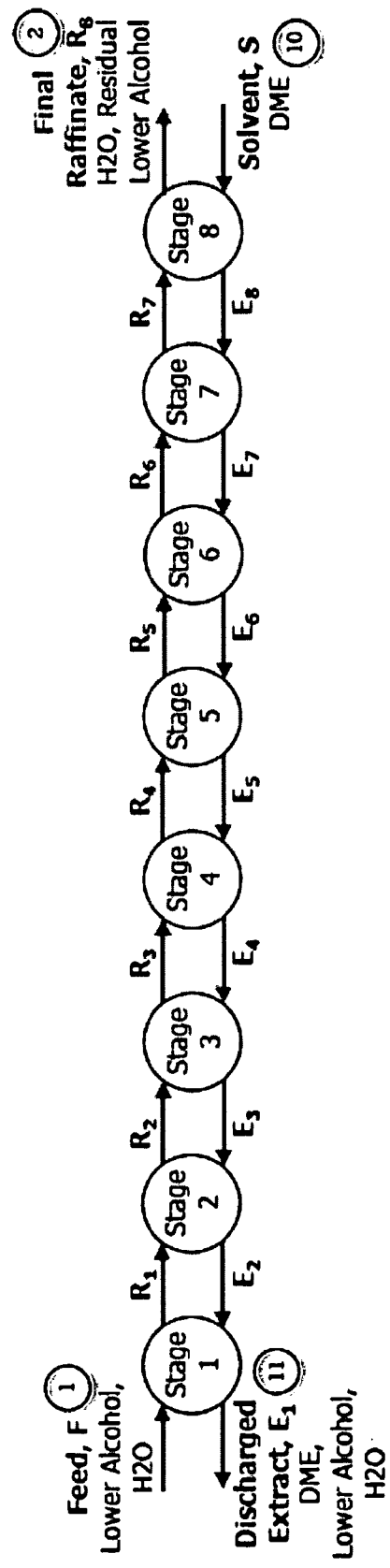

One illustrative embodiment for the concentration of dilute concentrations of butanol from an aqueous solution, e.g, a fermentation broth, is provided in FIG. 2. An aqueous solution, e.g, a fermentation broth, comprising less than about 5% butanol (e.g., from about 0.1% to about 3% butanol) is contacted with liquid phase DME at about a 1.0:1 solvent to feed ratio in a countercurrent column maintained at a pressure of about 8 bar and at a temperature of about 38° C. The DME is mixed with the dilute BuOH aqueous solution in sequential countercurrent columns, extracting the BuOH into the DME over 5-7 liquid-liquid extraction stages.

The aqueous phase comprising DME saturated with BuOH is delivered to a flash column and exposed to a flash temperature in the range of about 110-130° C. to remove the DME by vaporization. The vaporized DME is condensed back to liquid phase for recycling and reuse. The vaporization and condensation of DME is driven by a refrigeration circuit, e.g., using the refrigerant R134a. Residual DME remaining in the concentrated BuOH after flash vaporization can be removed by distillation. Under these parameters, it is possible achieve greater than 90% recovery and a 15-fold concentration of the BuOH from the feedstock aqueous solution with an energy input of less than about 3000 BTU/lb BuOH recovered, for example, less than about 2900 BTU/lb BuOH recovered, for example, an energy input in the range of about 2400-2900 BTU/lb BuOH recovered.

DME is recovered from the aqueous phase comprising unextracted BuOH (i.e., the raffinate) by reducing pressure (e.g., to about 300 torr; 0.4 atm; 0.4 bar; 5.8 psi), thereby vaporizing the DME in the aqueous raffinate. Residual DME in the aqueous raffinate, about 6%, can be returned to the fermenter (after sterilization). Raffinate returned to the fermentation medium comprises a portion of the total fermentation medium such that the total concentration of DME in the fermentation medium is less than 3 wt. %, for example less than 2 wt. % or less than 1 wt. %.

3. Systems for Extracting Biomolecules from Dilute Aqueous Solution

FIG. 1 shows one embodiment of a system for extracting a biomolecule from a dilute biomolecule-water solution. The system comprises a liquid feed inlet for receiving the biomolecule-water solution, an extraction vessel configured to extract the biomolecule(s) of interest with DME, a vaporizer for converting the DME to vapor phase, a collector configured to receive the concentrated biomolecule, a condenser for converting the vapor phase DME back to liquid phase, and a refrigerant circuit to drive the vaporization and condensation of DME in an energetically efficient manner.

The system of the present invention extracts biomolecule from a dilute biomolecule-water solution comprising less than 10 wt. % biomolecule, e.g., in the range of about 0.1 wt. % to about 10 wt. % biomolecule. In preferred embodiments, the systems of the invention allow for a continuous flow process, wherein materials are continuously flowing from one step of the system to the next. The systems preferably allow for the recycling and reuse of the DME solvent, and multiple iterations or stages of biomolecule concentration to achieve an aqueous solution with a biomolecule concentration greater than a target threshold concentration. The recycling and reuse of materials provides several energy savings. Additional energy savings stem from the lack of a distillation step in the concentration of dilute concentrations of the biomolecule of interest. Instead of an energy inefficient process such as distillation, the present invention uses liquid DME to extract the biomolecule. The DME-containing biomolecule is then vaporized to separate the biomolecule, followed by recondensation of the DME in order to recycle and reuse the DME. Accordingly, the system of the present invention provides an energy efficient process for extracting biomolecule(s) of interest from a dilute biomolecule-water solution.

As discussed above, the biomolecule-water solution can be a fermentation broth or beer, for example, from the fermentation of fruits and/or vegetables, or an ABE solution. In particular, corn is useful to prepare the fermentation broth of the present invention. In this case, ethanol is extracted from the ethanol-water solution using DME.

The dilute biomolecule-water solution is provided to the system of the present invention via a liquid feed inlet, for example, piping, hosing, tubing or reservoirs. One of skill in the art will appreciate that other input means find use. The biomolecule-water solution can be fresh feedstock, for example, from the fermentation broth, and/or can be from recycling biomolecule-water solution that has been subject to at least one iteration of concentration.

The feedstock biomolecule-water solution is placed in an extraction vessel where the biomolecule-water solution is contacted with liquid phase DME. The DME is in a phase such that the distribution coefficient for biomolecule in the biomolecule-water solution favors the transfer of the biomolecule from the water to the DME, thereby facilitating extraction and concentration of the biomolecule in the DME. The phase of the DME can be controlled by the appropriate selection of temperature and pressure. In preferred embodiments, the liquid phase DME is used at a pressure and temperature that is not close to the critical point for DME (53.405 bar and 127.15° C.). In some embodiments, DME extraction and concentration of biomolecule is performed at a temperature in the range of about 20° C. to about 35° C. and at a superambient pressure of less than 10 bar, for example in the range of about 3 to 5 bar.

The biomolecule is extracted into the DME using any known means in the art. For example, the biomolecule can be extracted by the DME using countercurrent column (CC) liquid-liquid extraction (LLE). Within the CC, one can consider that three processes are occurring in conjunction: mixing, coalescing, and separation. Mixing of the phases allows the interface between them to have a large area, and the analyte can move between the phases according to its partition coefficient. Within the countercurrent column, the biomolecule-water phase moves down the column and the DME-rich phase rises within the column. After passage through the countercurrent column, the biomolecule-water phase has been partially depleted of biomolecule and the DME-rich phase has been enriched with biomolecule. The depleted biomolecule-water phase can be returned for blending with feedstock dilute biomolecule solution. All or a portion of the biomolecule-enriched DME-rich phase can be subject to vaporization to separate the biomolecule from the DME. In some embodiments, this DME stream can be reintroduced into the column through a reflux valve. The recycling of the DME allows the DME to be reused and increases the efficient use of the DME.

The DME is then separated from the biomolecule in a vaporizer, by converting the DME to the vapor phase and collecting concentrated biomolecule in water in a collector. Vaporization is accomplished by changing the temperature and pressure in order to change the DME from the liquid phase to the vapor phase.

DME that has been vaporized can be recycled by first condensing the vaporized DME using a condenser by again changing the temperature and pressure in order to change the DME from vapor phase to liquid phase. Condensation of the DME is followed by reinjecting the DME into the extraction vessel. The recycling of the DME allows the DME to be reused, and minimizes the energy required for the extraction by minimizing materials used and energy consumed. The inclusion of a heat pump or refrigerant circuit to drive the vaporization and condensation of DME provides added energy efficiencies in the recycling and reuse of DME.

EXAMPLES

The following examples are offered to illustrate, but not to limit the claimed invention.

Example 1

Extraction of Dilute Ethanol and Acetone-Butanol-Ethanol (ABE) from Aqueous Solution Using Liquid Phase Dimethyl Ether (DME)

Experimental Set-Up

This example shows the effectiveness of liquid dimethyl ether to remove ethanol from water at initial concentrations of 2% and 4%, and in another test to remove acetone-butanol-ethanol from a typical "ABE" solution.

The tests were carried out in a 50-inch long by 0.68-inch internal diameter (ID) column containing stainless steel distillation packing to increase mass transfer between the liquid DME and the aqueous solution. The flow rate of the liquid DME for all the tests was about 20 SL/min, which calculates to a superficial velocity of the liquid DME of ~0.3 cm/sec.

Figure 3:
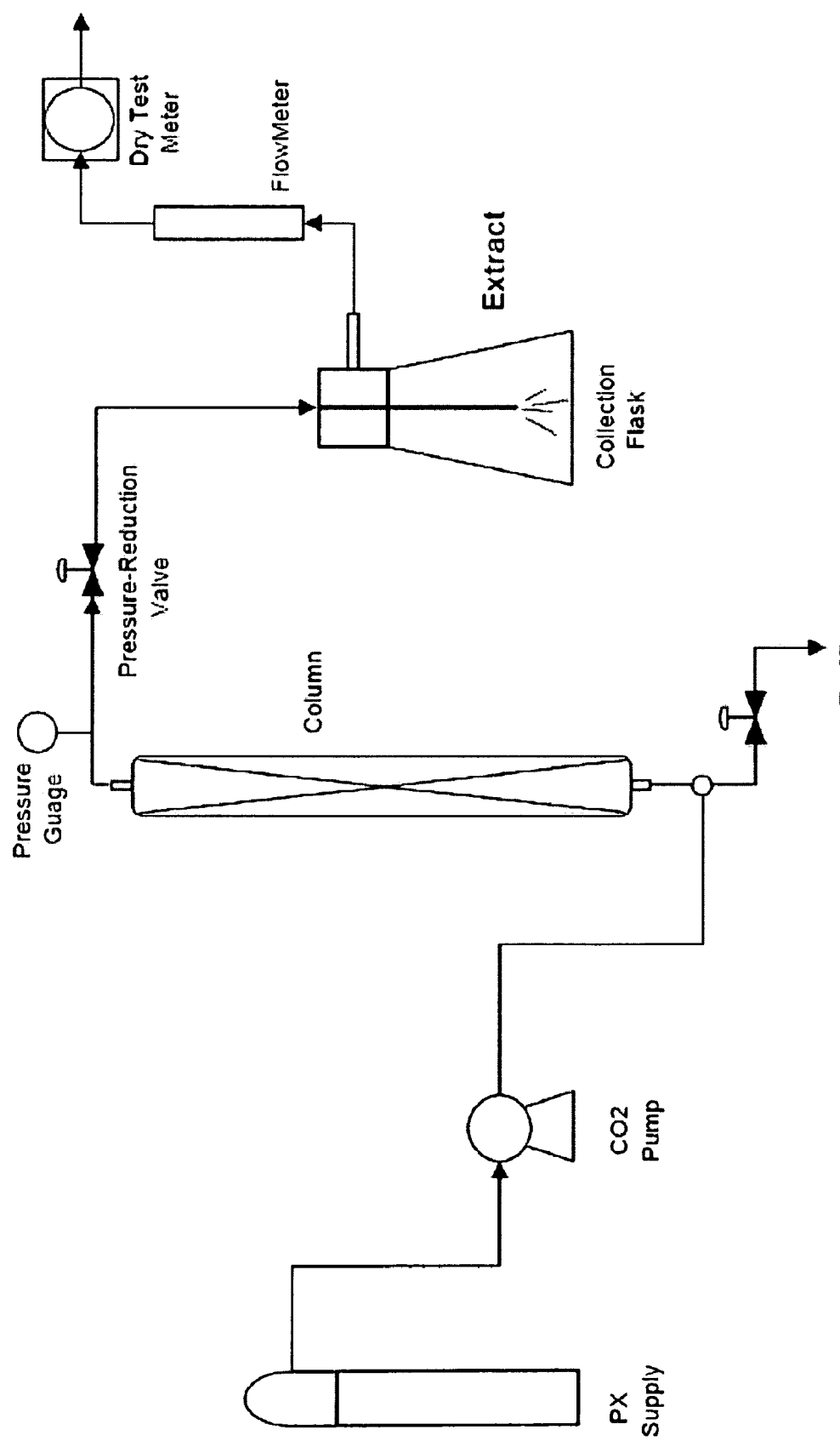
FIG. 3 illustrates a simplified set-up of the equipment used in Example 1.
Figure 4:
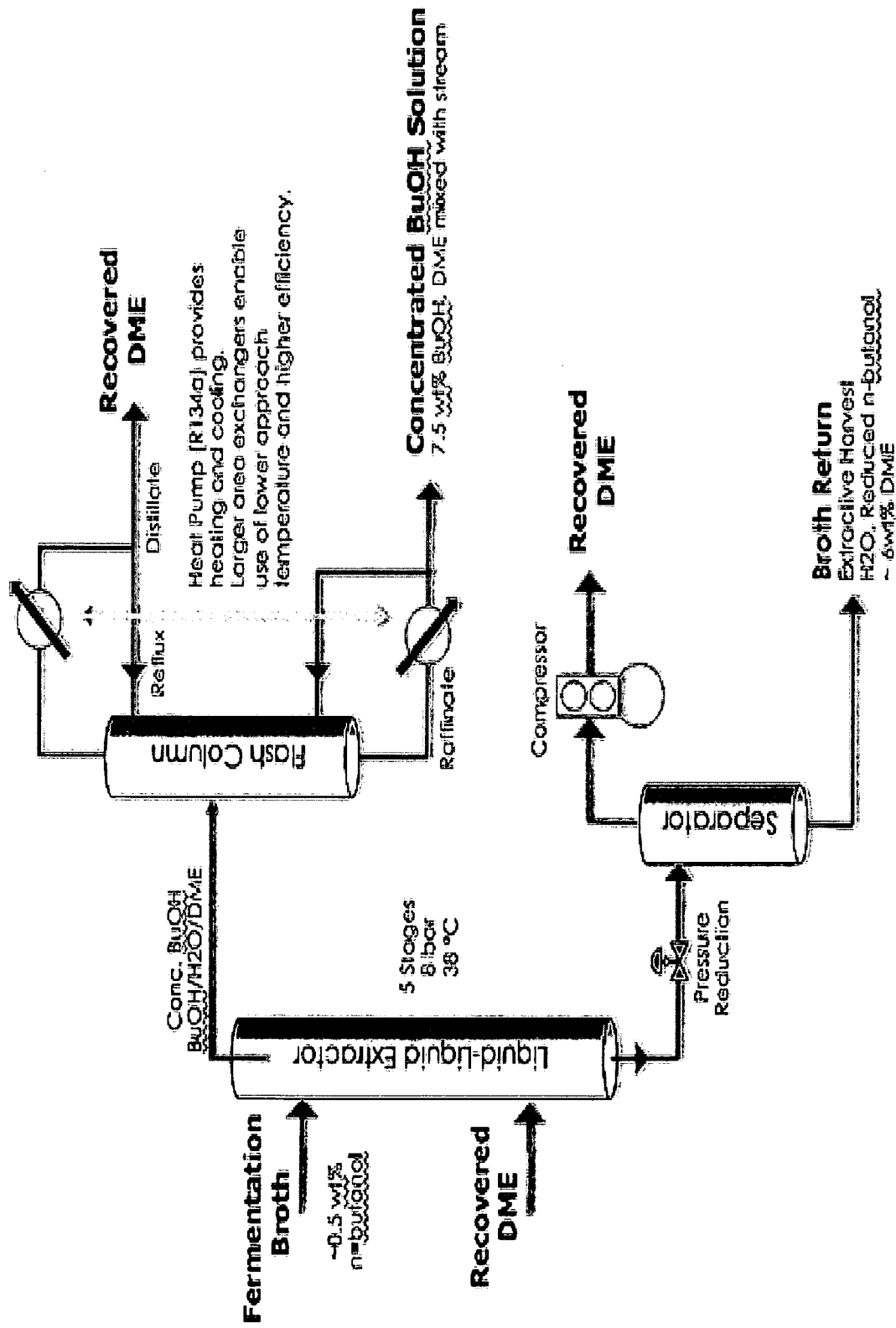
FIG. 4 illustrates a schematic for continuous flow, energy efficient concentration of lower alcohols (e.g., butanol) from aqueous solution using DME liquid-liquid-extraction. In relation to the schematic of FIG. 1, this schematic shows the downstream operations from the LLE (Liquid-liquid extraction) column to separate the liquid from the DME vapor. This schematic shows an embodiment where the heat pump would be employed (e.g., for recovering the DME from the concentrated BuOH stream).

FIG. 3 shows the simplified schematic set up of the equipment used for the tests summarized in this example.

For each test, about 65 g of a pre-made feed solution was charged to the extraction column, and the column was sealed. DME was introduced into the system and pressure was maintained at 250 psi with the lab pump. Each run was carried out at ambient temperature (about 30° C.), and flow was manually controlled with the pressure-reduction valve.

About ⅓ of the charge was extracted in each test with DME in three fractions, and the raffinate was collected at the end of each test in two fractions. In the event that the concentration of ethanol, or ABE, in the raffinate was not homogeneous along the length of the column, the raffinate was collected in two fractions where RAF#1 was the first (bottom) portion of the raffinate drained and RAF#2 was the remaining (upper) portion.

All samples along with controls were sent to R.D. Laboratories (Washington, Mo.) for gas chromatography (GC) analysis.

Results and Discussion

Two tests were carried out with ethanol-water solutions with ethanol at 2 wt. % and 4 wt. % concentrations in the feed. The tables below show the material balance and analytical results for each test.

TABLE 1

2 wt. % Ethanol Feed Concentration

| Fraction | Wt (g) | Wt % of charge | DME (g) | Wt % Solubility (w/w extract/DME) | Incremental S/F | Conc. Ethanol (wt %) |
|---|---|---|---|---|---|---|
| Control (Charge) | 64.7 | — | — | — | — | 2.15* |
| F1 | 7.79 | 12.0 | 84 | 9.2 | 1.3 | 6.63 |
| F2 | 5.84 | 9.0 | 56 | 10.4 | 0.9 | 5.57 |
| F3 | 5.98 | 9.2 | 56 | 10.7 | 0.9 | 3.19 |
| RAF 1 | 13.3 | 20.6 | — | — | — | 0.06 |
| RAF 2 | 26.8 | 41.4 | — | — | — | 0.13 |
| % Total Recovery | | 92.2 | | | | |

*The weighed concentration of the feed was 2.16 wt. %

TABLE 2

4 wt. % Ethanol Feed Concentration

| Fraction | Wt (g) | Wt % of charge | DME (g) | Wt % Solubility (w/w extract/DME) | Incremental S/F | Conc. Ethanol (wt %) |
|---|---|---|---|---|---|---|
| Control (Charge) | 65.4 | — | — | — | — | 4.04* |
| F1 | 11.21 | 17.1 | 84 | 13.3 | 1.3 | 11.11 |
| F2 | 6.45 | 9.9 | 56 | 11.5 | 0.9 | 7.73 |
| F3 | 6.75 | 10.3 | 56 | 12.1 | 0.9 | 3.94 |
| RAF 1 | 16.97 | 25.9 | — | — | — | 0.06 |
| RAF 2 | 11.85 | 19.1 | — | — | — | 0.10 |
| % Total Recovery | | 81.3 | | | | |

*The weighed concentration of the feed was 4.20 wt. %

TABLE 3

Acetone-Butanol-Ethanol Feed Solution

| Fraction | Wt (g) | Wt % of charge | DME (g) | Wt % Solubility (w/w extract/DME) | Incremental S/F | A acetone | B butanol | E ethanol |
|---|---|---|---|---|---|---|---|---|
| Control (Charge) | 71.66 | — | — | — | — | 0.21 | 0.50 | 0.09 |
| F1 | 6.7 | 9.3 | 75 | 8.9 | 1.0 | 0.52 | 2.91 | 0.40 |
| F2 | 5.19 | 7.2 | 56 | 9.3 | 0.8 | 0.31 | 0.84 | 0.29 |
| F3 | 5.47 | 7.6 | 56 | 9.7 | 0.8 | 0.08 | 0.10 | 0.15 |
| RAF 1 | 15.62 | 21.8 | — | — | — | ND | ND | ND |
| RAF 2 | 33.95 | 47.3 | — | — | — | ND | ND | ND |
| % Total Recovery | | 93.2 | | | | | | |

*The weighed concentration of the feed: A = 0.022 wt. %, B = 0.050 wt. 5, E = 0.11 wt. %

The distribution coefficient (DC) is calculated as the ratio of the concentration of the component in the extract (y) phase to the concentration of the component in the raffinate (x) phase, or DC=Cy/Cx. Using the material balance information in the tables above, and the component analysis supplied by R.D. Labs, the incremental DCs for each fraction were calculated. These DCs are calculated using the conservative assumption that there is no dissolved DME in the liquid phase remaining in the extractor. The DCs would increase by about 30% if it was assumed that the liquid phase in the extractor has about 30% dissolved DME.

The table below shows the calculated DCs for each fraction from the 2% EtOH and 4% EtOH tests.

TABLE 4

DC for Ethanol Solutions Extracted with Liquid DME

| Test | Fraction | Distribution Coefficient |
|---|---|---|
| 2% EtOH | F1 | 0.37 |
| 2% EtOH | F2 | 0.49 |
| 2% EtOH | F3 | 0.39 |
| 4% EtOH | F1 | 0.51 |
| 4% EtOH | F2 | 0.42 |
| 4% EtOH | F3 | 0.27 |

The following table shows the calculated DCs for each fraction and each of the three components from the ABE extraction test.

TABLE 5

DCs for ABE Solution Extracted with Liquid DME

| | Distribution Coefficient | | |
|---|---|---|---|
| Fraction | Acetone | Butanol | Ethanol |
| F1 | 0.24 | 0.95 | 0.57 |
| F2 | 0.16 | 0.36 | 0.65 |
| F3 | 0.04 | 0.04 | 0.50 |

Example 2

Energy Efficient Approach for Extraction of Lower Alcohols from Dilute Solution

Distribution coefficients (DC) were measured for aqueous mixtures of acetone, butanol and ethanol (ABE) using dimethyl ether (DME) as an extracting solvent with particular focus on butanol. The compositions of the aqueous mixtures were based on concentrations typically produced in a cellulosic fermentation. Surprisingly, the distribution coefficients were found to be several times larger than initially measured. Temperature was also varied between 30° C. and 38° C. but no significant change in DC was observed.

Procedure

Mixtures were charged to a pressure vessel and agitated to provide adequate contacting between the aqueous and solvent (DME) phases. Heat tape was used to control the temperature of the liquid that was measured by thermocouples. Pressure and temperature measurements were taken every five minutes. After temperature and pressure stabilization agitation was ceased and the liquid phases were allowed to fully settle. The two liquid phases were then separated, reduced to atmospheric pressure, collected and analyzed by HPLC for butanol, ethanol and acetone content.

Butanol DC.

Figure 5:
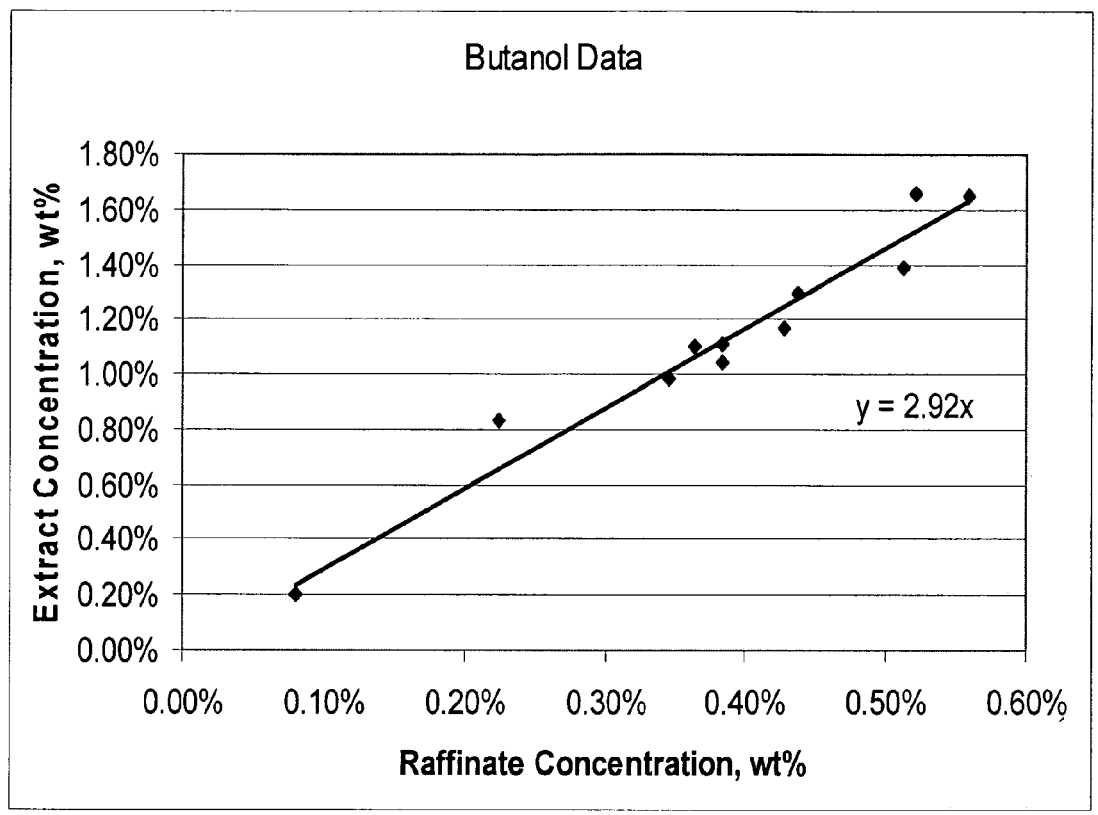
FIG. 5 illustrates a plot of the butanol concentration in the extract versus raffinate. The slope of the line fit is equal to the distribution coefficient (DC).

The distribution coefficient of butanol was measured over a range of extract and raffinate compositions. FIG. 5 shows a plot of extract concentration versus raffinate concentration. The slope of the linear line fit is equal to the DC. The linear line fit accurately models the data and shows that the distribution coefficient for butanol is constant over the given concentration range. The DC was measured as 2.9 which is significantly higher than previous results which measured the DC to be approximately one.

Effects of Temperature.

Figure 6:
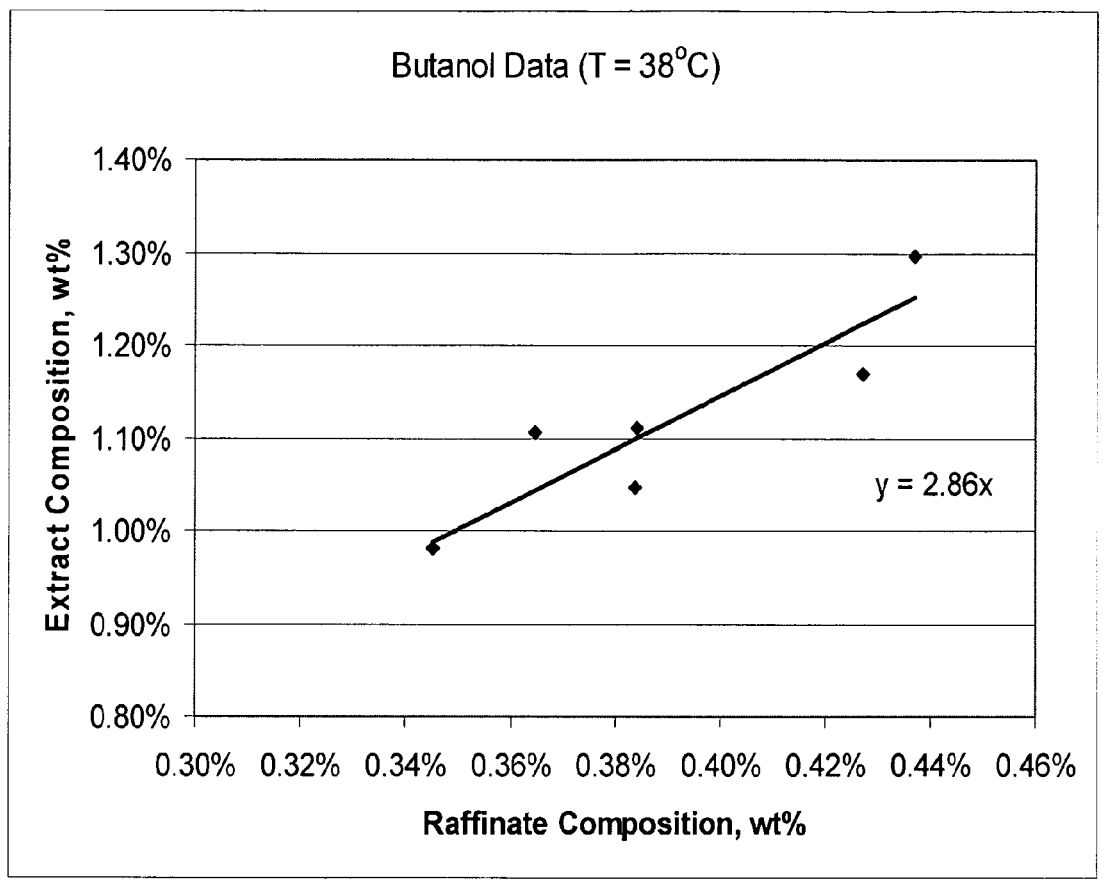
FIG. 6 illustrates butanol extraction data at 38° C. The DC is given by the slope of the line fit and is equal to 2.86.
Figure 7:
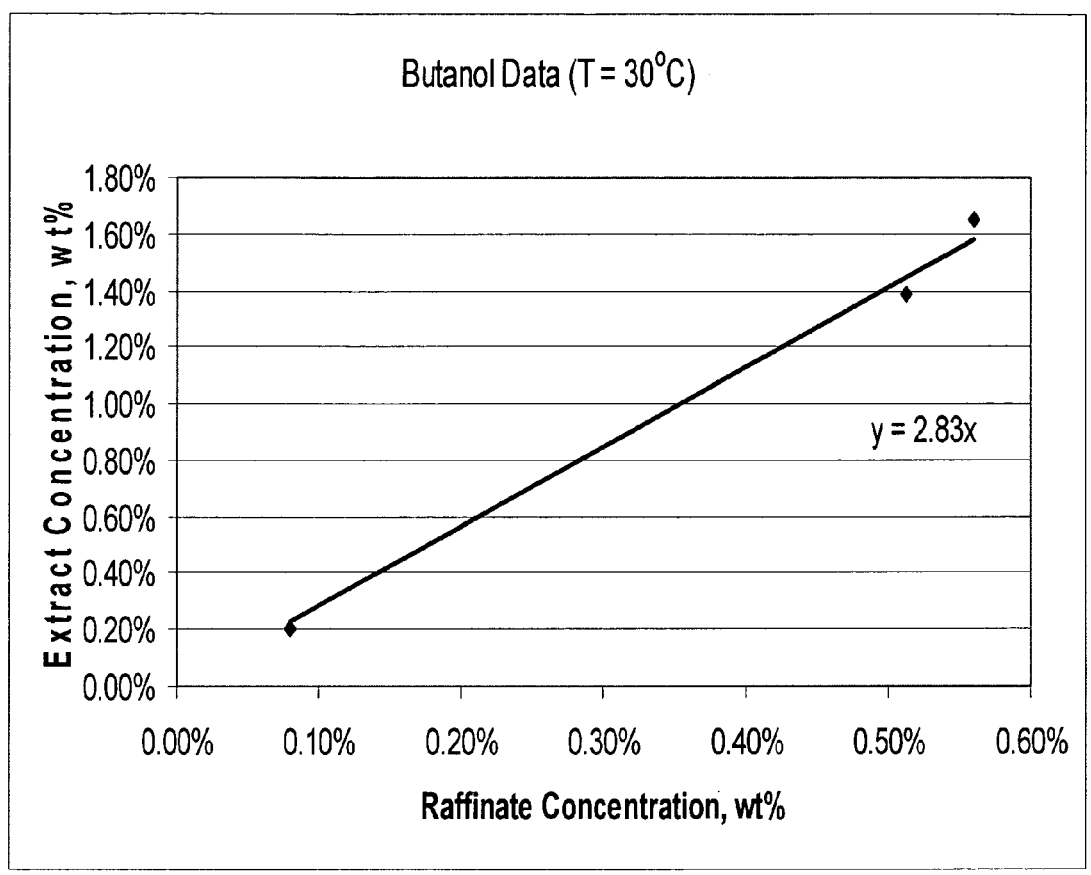
FIG. 7 illustrates a graph of butanol data at 30° C. The distribution coefficient is given by the slope of the graph and is equal to 2.83. This is approximately the same result obtained at 38° C. indicating the data does not support a strong temperature dependence on the distribution coefficient.

The distribution coefficient for butanol was measured at 31° C. and 38° C. This was done to see if there was a substantial change in the DC with temperature. The temperature range was also chosen to include the typical fermentation temperature of 38° C. FIGS. 6 and 7 show the plots of butanol concentration in the extract vs. raffinate for the two temperatures. The slope of the linear fit is equal to the DC. Based on the data in FIGS. 6 and 7, the distribution coefficient was measured as 2.83 and 2.86 at 30° C. and 38° C. The close agreement with DC measurements at the two temperatures suggests there is not a strong temperature dependence on DC within the range of 30° C.-38° C.

Ethanol Distribution Coefficient.

Figure 8:
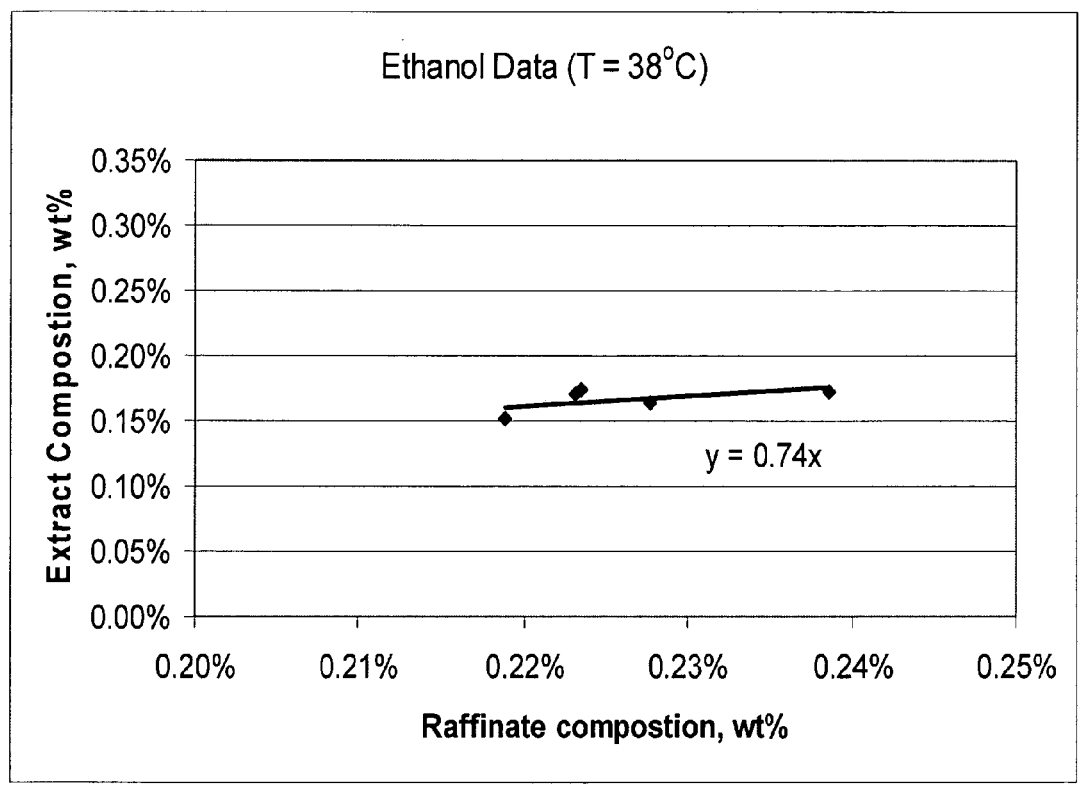
FIG. 8 illustrates data used to calculate the distribution coefficient of ethanol as 0.74. The current measurement is approximately 30% larger than previous measurements.

The distribution coefficient for ethanol in ABE and BE mixtures was measured at 38° C. The data obtained is plotted in FIG. 8. The data shows the ethanol distribution coefficient is equal to 0.74. This is slightly higher than previous measurements that had an average of 0.57.

Acetone Distribution Coefficient.

Figure 9:
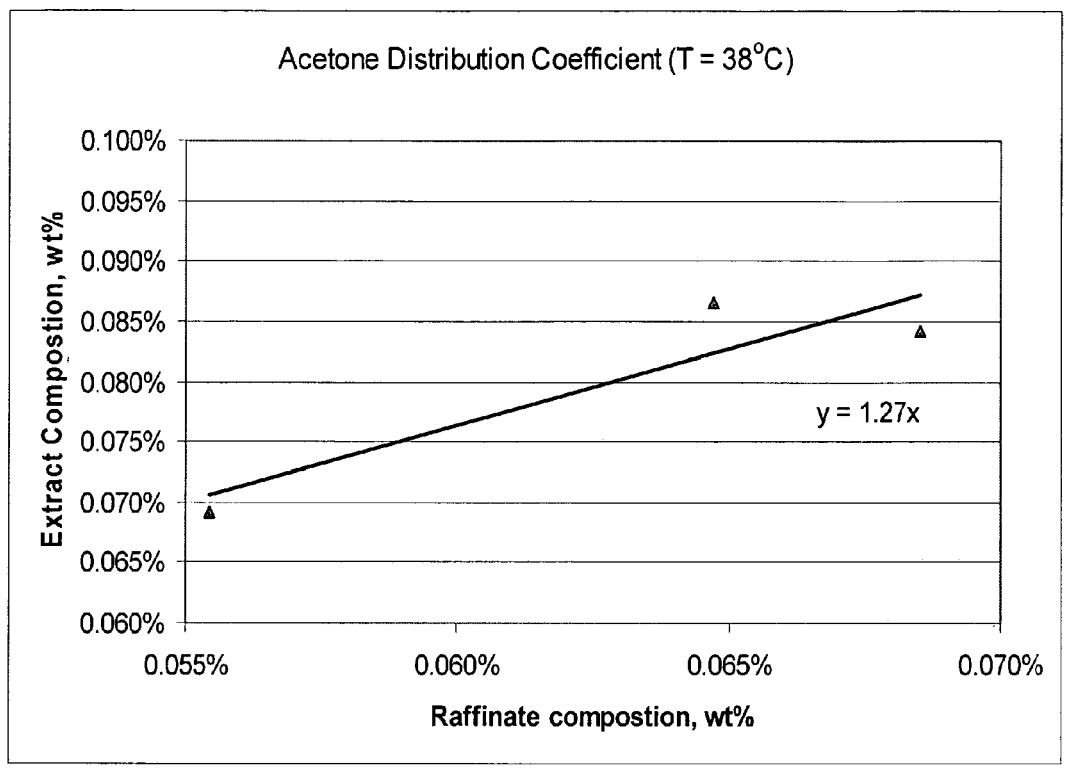
FIG. 9 illustrates data used to calculate the distribution coefficient of acetone at 38° C. The current value of the distribution coefficient is 1.27 that is approximately four times larger than previously measured.

Measurements on acetone concentration were also made during the extraction experiments. The data collected is presented in FIG. 9. The calculated distribution coefficient was measured as 1.27. This is approximately five times larger than the previously measured value of 0.25.

Summary of Extraction Experiments

A summary table of all data obtained in the extraction experiments is given in Table 6, which shows measured distribution coefficient (DC), extract compositions, raffinate compositions and component mass balances (MB). Data in the table has been used in FIGS. 5-9 for obtaining a linearly regressed value for distribution coefficient. The summary table also shows the distribution coefficient measured for each experiment as well as the extract and raffinate compositions used to calculate the DC for each experiment. A mass balance was also performed on each component of the ABE and BE mixtures to determine a degree of accuracy of the results.

The mass balance for the butanol and ethanol is on average 91 wt. % and 95 wt. % respectively. The only measurement that varies widely from these averages is the ethanol mass balance on BE3. For this reason the ethanol data was treated as an erroneous data point and was not used for distribution coefficient calculations.

The acetone mass balance averaged 78 wt. %. The lower degree of mass balance can be attributed to the lower concentration that makes it highly sensitive to small amounts of measurement error.

TABLE 6

Summary Of Extraction Data Used To Determine Distribution Coefficients

| Component | Extraction Test | ABE1 | ABE2 | ABE3 | ABE4 | BE1 | BE2 | BE3 | BE3 | B1 | B2 | B3 |
|---|---|---|---|---|---|---|---|---|---|---|---|---|
| | Temperature, ° C. | 31.1 | 38.3 | 38.3 | 38.0 | 30.1 | 38.9 | 37.6 | 38.4 | 27.0 | 28.2 | 29.6 |
| | Pressure, psig | 104 | 102 | 103 | 103 | 85 | 107 | 103 | 106 | 78 | 83 | 86 |
| Butanol | DC | 2.95 | 2.72 | 2.74 | 2.97 | 2.70 | 2.84 | 2.89 | 3.03 | 3.17 | 3.71 | 2.49 |
| | Extract, wt. % | 1.65% | 1.05% | 1.17% | 1.30% | 1.38% | 0.98% | 1.11% | 1.11% | 1.65% | 0.83% | 0.20% |
| | Raffinate, wt. % | 0.56% | 0.38% | 0.43% | 0.44% | 0.51% | 0.35% | 0.38% | 0.36% | 0.52% | 0.22% | 0.08% |
| | MB | 94.6% | 89.2% | 90.0% | 91.2% | 92.6% | 91.8% | 92.4% | 93.7% | 91.1% | 83.5% | 88.9% |
| Ethanol | DC | 0.81 | 0.70 | 0.72 | 0.78 | 0.71 | 0.72 | 3.25 | 0.76 | | | |
| | Extract, wt. % | 0.20% | 0.15% | 0.16% | 0.17% | 0.17% | 0.17% | 0.72% | 0.17% | | | |
| | Raffinate, wt. % | 0.25% | 0.22% | 0.23% | 0.22% | 0.24% | 0.24% | 0.22% | 0.22% | | | |
| | MB | 95.4% | 93.8% | 97.5% | 96.9% | 93.7% | 94.5% | 204.0% | 93.6% | | | |
| Acetone | DC | 1.28 | 1.25 | 1.23 | 1.34 | | | | | | | |
| | Extract, wt. % | 0.09% | 0.07% | 0.08% | 0.09% | | | | | | | |
| | Raffinate, wt. % | 0.07% | 0.06% | 0.07% | 0.06% | | | | | | | |
| | MB | 81% | 78% | 77% | 78% | | | | | | | |
| Water | DC | 0.15 | 0.14 | 0.13 | 0.14 | 0.13 | 0.13 | 0.12 | 0.12 | 0.15 | 0.11 | 0.11 |
| | Extract, wt. % | 11% | 10% | 9% | 9% | 9% | 9% | 8% | 8% | 9% | 7% | 7% |
| | Raffinate, wt. % | 69% | 70% | 70% | 68% | 70% | 72% | 70% | 68% | 63% | 66% | 69% |

DC = Distribution Coeffient,
MB = Mass Balance

Example 3

Toxicity Studies

Toxicity studies were performed to determine the effects of DME on fermentation cultures. Cell growth, viability and solvent production were measured to determine what effect DME has on fermentation cultures. Cell growth was monitored by absorption measurements taken at 600 nm (A600). Viability was measured by counting the colony forming units (CFU) after 24 hours. Solvent production was quantified by HPLC.

Round One Measurements.

The first round of testing was performed using media that had been sparged with DME gas at 23° C. The amount of DME absorbed into the media was measured by weight gain after sparging. The concentration of DME in the media ranged from 2.96 to 3.92 wt. %. Two control cultures were also used for direct comparison of cultures with and without the presence of DME.

The results for the first round of testing are presented in Table 7. The Table shows that the control cultures 1-B and 2-B exhibited higher growth rates as indicated by the A600 measurements. This shows that media containing 3 to 4 wt. % DME causes a substantial reduction in cell growth. The solvent production in cultures containing DME was also greatly reduced as is evident by the ethanol, acetone and n-butanol concentration listed in Table 7 when compared with the control cultures. The effect of DME on cell viability was measured by the number of colony forming units (CFU) which had varying results. Cultures 1-2 and 1-3 had results comparable to the control indicating DME concentrations of approximately 3 wt. % were not toxic to these particular cultures. The second set of cultures had a low CFU value indicating toxicity issues at DME concentrations of approximately 4 wt. %.

TABLE 7

Data from DME Toxicity sSudies Performed at DME Concentration of 3 wt. % to 4 wt. %

| Culture | Weight % DME | Vessel from Previous worksheet | $A_{600}$ 4 hours | 7 hours | 22 hours | 28 hours | 196 hours | CFU/ml after 24 hours | Metabolite conc. Final (mM) Glucose | Acetate | Acetoin | Ethanol | Butyrate | Acetone | Butanol |
|---|---|---|---|---|---|---|---|---|---|---|---|---|---|---|---|
| 1B | 0% | — | 1.295 | 2.33 | 3.955 | 3.16 | 0.81 | 210000 | 340.03 | 51.72 | 12.75 | 4.34 | 42.51 | 14.64 | 27.70 |
| 1-1 | 3.70% | 6 | 0.184 | 0.241 | NG | 0.137 | 0.075 | 770 | 431.29 | 32.49 | 0.00 | 0.00 | 93.55 | 0.00 | 0.00 |
| 1-2 | 3.48% | 4 | 0.205 | 0.194 | NG | 0.175 | 0.39 | >10000 | 410.70 | 42.01 | 0.00 | 0.00 | 101.72 | 0.00 | 0.00 |
| 1-3 | 2.96% | 1 | 0.340 | 0.690 | 1.745 | 1.69 | 1.08 | 200000 | 380.17 | 47.46 | 0.00 | 0.00 | 89.52 | 8.33 | 14.84 |
| 2-B | 0% | — | 1.675 | 2.66 | 3.92 | 3.530 | 1.785 | 250000 | 219.16 | 45.36 | 46.36 | 11.11 | 27.00 | 56.44 | 105.84 |
| 2-1 | ? | 7 | 0.140 | 0.157 | NG | 0.072 | 0.05 | 0 | 432.02 | 33.46 | 0.00 | 0.00 | 94.00 | 0.00 | 0.00 |
| 2-2 | 3.92% | 3 | 0.173 | 0.178 | NG | 0.127 | 0.32 | 4480 | 418.43 | 42.17 | 0.00 | 0.00 | 91.28 | 0.00 | 0.00 |
| 2-3 | 3.72% | 2 | 0.230 | 0.159 | NG | 0.077 | 0.06 | 130 | 431.79 | 34.46 | 0,00 | 0.00 | 86.91 | 0.00 | 0.00 |

Round Two Measurements.

A second round of testing was performed at lower DME concentrations. The concentration of DME varied from 0.7 wt. % to 2.9 wt. %. Cell densities were measured between 3 and 64 hours after inoculation. Based on the data in Table 7 for cultures 2-2 and 2-3, DME concentrations below 0.7 wt. % did not appear to inhibit growth. Based on the solvent measurements in Table 8 and Table 9 solvent production was also unaffected by DME at 0.7 wt. %. DME concentrations above 1.6 wt. % showed some inhibition on growth and solvent production as is evident by the measurements made on cultures 1-1 and 1-2. Further increases in the DME concentration in the range of 2.5 to 3 wt. % caused a substantial decrease in growth and solvent production. This is apparent after examination of the cell density and solvent production for samples 1-5, 2-1, 2-4 and 2-5 in comparison to the control samples 1-B and 2-B.

TABLE 8

Metabolite Analysis On Cultures 36 Hours After Inoculation
Concentrations (mM) 36 hours after inculation

| Culture | DME Conc. (g/L) | Glucose | Acetate | Acetoin | Ethanol | Butyrate | Acetone | Butanol |
|---|---|---|---|---|---|---|---|---|
| 1-B | 0.0 | 351.6 | 48.0 | 16.3 | 4.4 | 45.7 | 11.1 | 23.8 |
| 1-1 | 16.0 | 379.0 | 47.4 | 0.0 | 2.4 | 69.9 | 5.9 | 15.9 |
| 1-2 | 18.1 | 387.7 | 46.2 | 0.0 | 1.0 | 76.2 | 3.8 | 11.7 |
| 1-3 | 19.4 | 389.1 | 45.3 | 0.0 | 0.0 | 79.0 | 2.9 | 9.7 |
| 1-4* | 43.8 | 384.9 | 45.9 | 0.0 | 0.0 | 75.9 | 3.3 | 10.5 |
| 1-5 | 25.8 | 403.3 | 43.6 | 0.0 | 0.0 | 86.4 | 2.3 | 6.2 |
| 2-B | 0.0 | 355.6 | 50.8 | 23.6 | 4.3 | 50.1 | 7.9 | 20.2 |
| 2-1 | 26.0 | 402.4 | 43.3 | 0.0 | 0.0 | 85.9 | 1.9 | 6.8 |
| 2-2 | 6.8 | 358.8 | 46.1 | 0.0 | 3.3 | 56.2 | 9.7 | 23.6 |
| 2-3 | 6.6 | 355.1 | 46.2 | 0.0 | 4.4 | 39.6 | 9.3 | 22.2 |
| 2-4 | 29.1 | 410.5 | 42.2 | 0.0 | 0.0 | 88.6 | 0.0 | 3.5 |
| 2-5 | 27.9 | 402.3 | 42.4 | 0.0 | 0.0 | 91.7 | 3.3 | 7.0 |

TABLE 9

Metabolite Analysis On Cultures 196 Hours After Inoculation
Concentration (mM) 196 hours after inocluation

| Culture | DME Conc. (g/L) | Glucose | Acetate | Acetoin | Ethanol | Butyrate | Acetone | Butanol |
|---|---|---|---|---|---|---|---|---|
| 1-B | 0.0 | 341.7 | 46.6 | 9.4 | 3.6 | 44.7 | 11.3 | 23.3 |
| 1-1 | 16.0 | 369.2 | 47.9 | 2.3 | 3.5 | 73.2 | 6.9 | 15.6 |
| 1-2 | 18.1 | 381.5 | 45.7 | 1.7 | 1.9 | 80.8 | 4.9 | 11.7 |
| 1-3 | 19.4 | 383.7 | 46.0 | 2.2 | 1.9 | 85.7 | 4.0 | 9.7 |
| 1-4* | 43.8 | 377.5 | 45.6 | 2.9 | 2.7 | 86.3 | 6.3 | 10.8 |
| 1-5 | 25.8 | 398.0 | 42.3 | 0.0 | 1.2 | 94.4 | 3.3 | 6.3 |
| 2-B | 0.0 | 348.4 | 49.7 | 12.4 | 3.5 | — | 8.6 | 20.2 |
| 2-1 | 26.0 | 399.2 | 42.5 | 0.0 | 0.0 | 91.1 | 2.9 | 6.7 |
| 2-2 | 6.8 | 354.4 | 46.2 | 5.0 | 3.8 | 55.7 | 10.2 | 23.6 |
| 2-3 | 6.6 | 338.3 | 44.6 | 5.6 | 3.8 | 57.3 | 9.6 | 21.6 |
| 2-4 | 29.1 | 403.0 | 42.5 | 0.0 | 0.0 | 94.8 | 2.1 | 3.7 |
| 2-5 | 27.9 | 396.9 | 41.7 | 0.0 | 0.0 | 94.5 | 4.3 | 7.2 |

TABLE 10

Cell Density Measurements Used To Determine Growth
Between 3 And 64 Hours After Inoculation

| Culture | DME Conc. (g/L) | A600 values | | | |
|---|---|---|---|---|---|
| | | 3 hours | 24 hours | 40 hours | 64 hours |
| 1-B | 0.0 | 0.629 | 3.850 | 2.83 | 2.19 |
| 1-1 | 16.0 | 0.349 | 3.070 | 2.66 | 2.12 |
| 1-2 | 18.1 | 0.523 | 2.565 | 1.82 | 1.97 |
| 1-3 | 19.4 | 0.463 | 2.695 | 2.16 | 2.15 |
| 1-4* | 43.8 | 0.807 | 3.005 | 1.95 | 2.14 |
| 1-5 | 25.8 | 0.543 | 1.415 | 1.28 | 1.26 |
| 2-B | 0.0 | 0.331 | 3.620 | 1.56 | 1.42 |
| 2-1 | 26.0 | 0.505 | 1.390 | 2.48 | 2.24 |
| 2-2 | 6.8 | 0.776 | 3.755 | 1.29 | 1.36 |
| 2-3 | 6.6 | 0.783 | 3.700 | 2.65 | 2.63 |
| 2-4 | 29.1 | 0.590 | 1.195 | 2.63 | 2.19 |
| 2-5 | 27.9 | 0.885 | 1.735 | 1.18 | 1.19 |

Conclusion.

Based on cell growth and solvent production measurements it appears DME levels below 0.7 wt. % do not have a noticeable effect on the cell cultures. As the DME concentration increased to approximately 1.6 wt. % growth and solvent production was partially inhibited. Growth and solvent production was more substantially inhibited as DME concentrations increased above 2.5 wt. %. Based on these findings it preferred to keep DME levels in recycled water below 0.7 wt. % to enable continuous cell growth in the presence of DME.

Example 4

Separation of DME from Fermentation Broth

DME Saturation Measurements.

The saturation concentration for DME dissolved in fermentation broth was measured at 25° C., 35° C. and 45° C. The solubility data are shown in FIG. 10. The data was obtained for sparging times of one, two and three minutes. The close agreement in measurements at 35° C. and 45° C. for the various sparging times indicates that an equilibrium concentration had been attained after two to three minutes.

The graph shows that at fermentation conditions of 38° C., the amount of DME in the broth was measured as ~2.3 wt. %. Toxicity studies indicate that concentrations of DME>2.5 wt. % severely inhibit growth and solvent production, concentrations of 1.6 wt % partially inhibit growth and butanol production and concentrations of <0.7 wt % have no observable effect on the cells. Based on these results it appears that the DME concentration in the extracted fermentation broth be returned to the bioreactor at or below concentrations of 0.7 wt %.

Aspen Plus Simulation and Energy Requirements.

Aspen Plus was used to determine the energy required to get the DME concentration to the innocuous level of 0.7 wt. %. This calculation focused on removal of the last couple percent of DME from the extracted fermentation broth (raffinate). A system operating under a pressure of 4.0 psia (0.3 atm, 206 torr) was chosen to lower the operating temperature and prevent a high temperature source from being required. Additionally, the temperature required at 206 torr is approximately equal to the fermentation temperature of 38° C.

Figure 11:
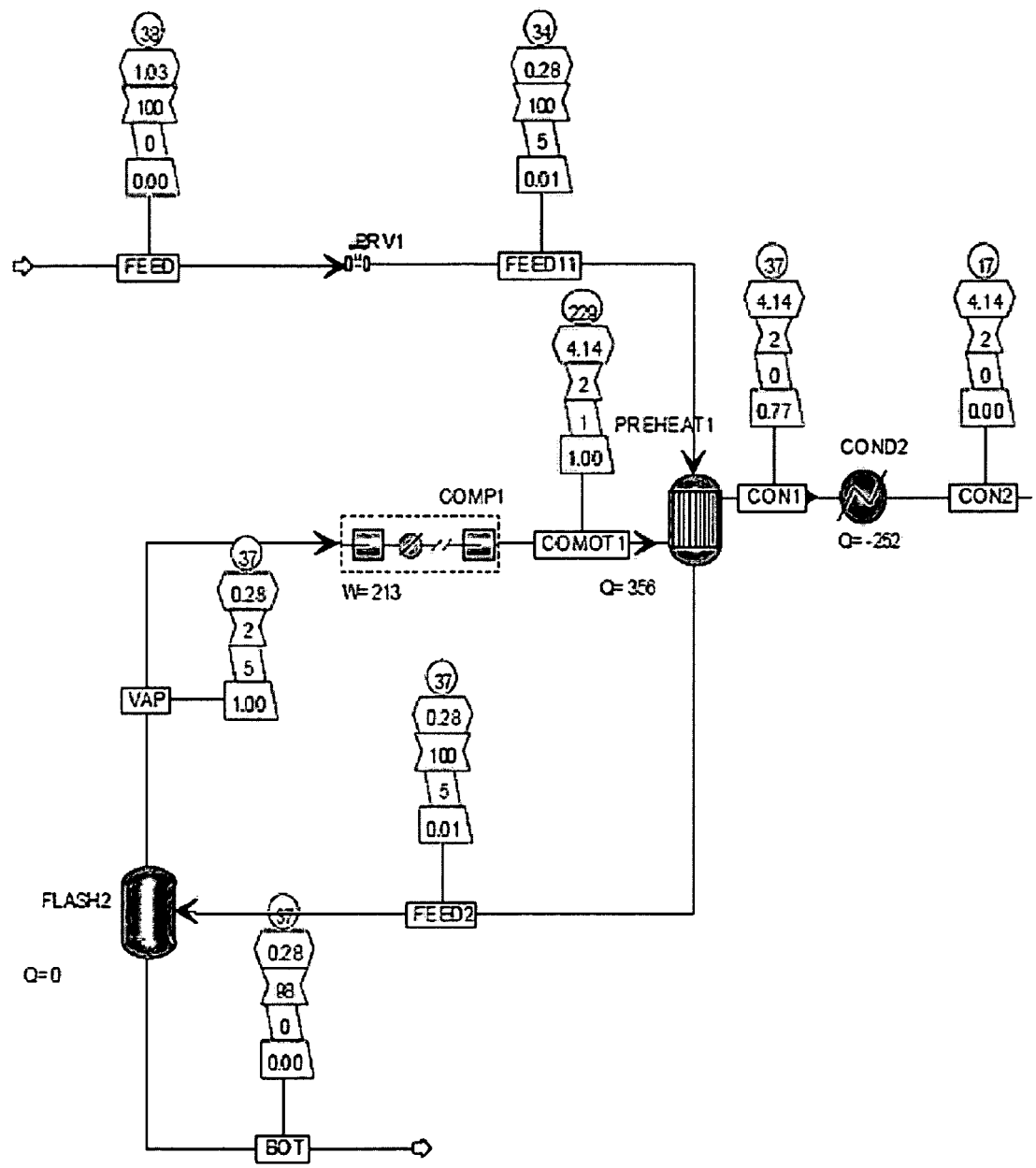
FIG. 11 illustrates an Aspen model of vapor recompression process used to achieve low levels (<0.7 wt %) of DME in media returned to the bioreactor.

The process to remove the DME from the fermentation broth was modeled as a vapor recompression process. The Aspen model is shown in FIG. 11. This process was chosen so that the heat generated from compressing the DME from vacuum to extraction pressures could be recovered and used to drive the removal of DME from the fermentation broth. At a pressure of 206 torr and a temperature of 37° C., the DME level in the extracted fermentation broth was found to be 0.6 wt. %. This is below the DME concentration of 0.7 wt. % that was determined to have no noticeable effect on the solvent production.

The Aspen model was based on a flow rate of 100 kg/hr with a composition of 2.5 wt. % DME and 97.5 wt. % water. Based on an original broth composition of 1.8 wt. % n butanol, the 97.5 kg/hr of water exiting the extractor correlates to 1.79 kg/hr of n butanol product. The energy required for the separation was in the form of the compressor power and was 213 Watts. On a unit n butanol product basis, it is 428 kJ/kg (102 kcal/kg). The stream table documenting mass flows for the Aspen Plus model is shown in Table 11.

TABLE 11

Stream Table Results From Aspen Plus
Documenting Mass Flows For The Process Model

| | | \multicolumn{8}{c}{Stream Name} | | | | | | | |
|---|---|---|---|---|---|---|---|---|---|
| | | BOT | COMOT1 | CON1 | CON2 | FEED | FEED2 | FEED11 | VAP |
| Temperature | °C. | 37 | 228.8 | 36.9 | 16.9 | 37.8 | 37 | 34.1 | 37 |
| Pressure | Atm | 0.3 | 4.1 | 4.1 | 4.1 | 1.0 | 0.3 | 0.3 | 0.3 |
| Vapor Fraction | | 0 | 1 | 0.77 | 0 | 0 | 0.01 | 0.01 | 1 |
| Mass Flow | kg/hr | 97.608 | 2.182 | 2.182 | 2.182 | 99.79 | 99.79 | 99.79 | 2.182 |
| Volume Flow | l/hr | 100 | 548 | 248 | 3 | 102 | 5227 | 4764 | 5127 |
| WATER | kg/hr | 97.07 | 0.23 | 0.23 | 0.23 | 97.30 | 97.30 | 97.30 | 0.23 |
| DME | kg/hr | 0.54 | 1.96 | 1.96 | 1.96 | 2.50 | 2.50 | 2.50 | 1.96 |
| WATER | wt. % | 99.4% | 10.4% | 10.4% | 10.4% | 97.5% | 97.5% | 97.5% | 10.4% |
| DME | wt. % | 0.6% | 89.6% | 89.6% | 89.6% | 2.5% | 2.5% | 2.5% | 89.6% |

Conclusion.

Concentrations of DME below 0.7 wt. % during fermentation were shown to have no noticeable effect on cell growth and solvent production. The process required to achieve DME concentrations below 0.7 wt. % was modeled in Aspen Plus. The process requires the use of vacuum at 4 psia (206 torr) and a temperature of 37° C., a vacuum and temperature level that could be readily achieved with commercial off the shelf (COTS) apparatus. Under these conditions the DME level was 0.6 wt. % and the amount of energy required was 428 kJ/kg (102 kcal/kg) butanol product. This is a small energy component relative to that necessary to evaporate the bulk DME via a heat pump enhanced evaporation, conventional vapor recompression distillation, or gas stripping.

Example 5

Continuous Counter Current Column (CCC) Extraction of Acetone, Butanol and Ethanol (ABE) from a Dilute Aqueous Solution Using DME A continuous counter current column (CCC) was designed and built for the extraction of acetone, butanol and ethanol (ABE) from a dilute aqueous solution using DME as the extracting solvent. The column was complete with a DME recovery operation to reuse most of the solvent in a closed recirculation loop. Temperatures, pressures and flow rates were recorded during column operation. Periodic extract and raffinate samples were taken and analyzed for ABE content.

The extraction column operated at a temperature of 37° C. and 24° C. at the top and bottom of the column respectively. The n-butanol concentration of the ABE feed was 1.8 wt. %. The average concentration of the extract samples produced during operation of the CCC was 17.6 wt. % n-butanol. The high concentration of butanol in the extract resulted in the formation of a concentrated butanol liquid phase that was 80 wt. % butanol. This highly concentrated butanol phase could be easily decanted from the aqueous liquid phase.

Apparatus.

Figure 12:
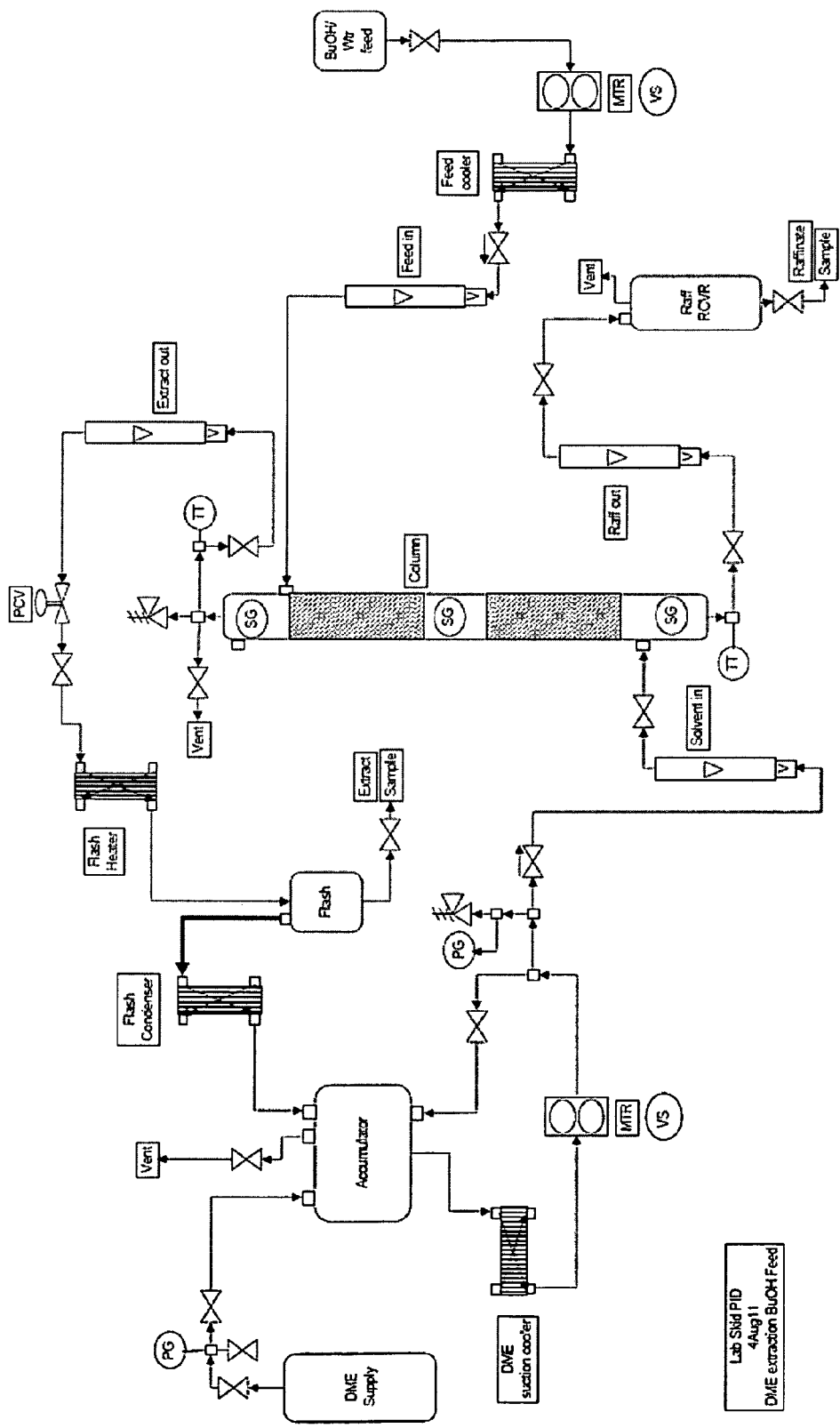
FIG. 12 illustrates the Process and Instrumentation Diagram (P&ID) of the counter current column test unit.

A basic diagram of the CCC apparatus is provided in FIG. 12 below. The column was constructed out of 1.5" sanitary tubing and was packed with stainless steel mesh. The column was complete with several sight glasses to observe the liquid-liquid interface and to observe liquid droplet size and velocity. The column operates with the dilute ABE solution entering at the top of the column and exiting as ABE depleted raffinate at the bottom of the column. The solvent (DME) enters the bottom of the column and flows passed the ABE solution and exits the top of the column as extract. Flow meters were located at all inlets and outlets of the CCC and thermocouples were located at the top and bottom of the column.

Two gear pumps were used to pump the ABE feed and extracting solvent to the column. Needle valves were used on the extract and raffinate streams to the control pressure and meter flow from the column to maintain steady mass balance. The extract exiting the column flows through a heater to evaporate the DME that then flows into a flash tank to separate the DME vapor from the liquid ABE extract. The DME is then condensed and recycled. The raffinate exiting the column went to a flash tank where DME vapor was separated from the liquid raffinate. ABE Extract and raffinate were sampled from their respective flash tanks during testing to monitor ABE concentrations.

Data Collection.

The data reported here is for a stable run using a mass solvent to feed ratio (S/F) of 0.9. The run was performed with precision control valves allowing for accurate control of pressure and flow rate. A temperature gradient of approximately 12.8° C. was noticed during column operation. This temperature gradient was the result of the exothermic heat of mixing from combining DME and water. Over the course of the run the top and bottom column temperatures averaged 36.9° C. and 24.1° C. respectively. The data for flow, temperature and pressure of the CCC are presented in Table 12.

TABLE 12

Run Sheet for Continuous Countercurrent Column (CCC) Testing

| | Extractor Conditions | | | Flow Rates | | | | Pump Speed | | DME Recycle Pressure | | Utilities | |
|---|---|---|---|---|---|---|---|---|---|---|---|---|---|
| Time | Pressure psi | Top Temperature °C. | Bottom Temperature °C. | ABE Flow g/min | DME Flow g/min | RAF Flow g/min | Extract Flow g/min | DME Drive Hz | ABE Drive Hz | Condenser psig | Accumulator psig | Heater Temperature °C. | Chiller Temperature °C. |
| 0 | 110 | 34.5 | 20.7 | 184 | 154 | 244 | 122 | 24.5 | 37.9 | 65 | 65 | 45 | 10.0 |
| 5 | 110 | 36.1 | 22.3 | 172 | 137 | 205 | 132 | 25.4 | 37.9 | 62 | 62 | 45 | 10.7 |

TABLE 12-continued

Run Sheet for Continuous Countercurrent Column (CCC) Testing

| | Extractor Conditions | | | Flow Rates | | | | Pump Speed | | DME Recycle Pressure | | Utilities | |
|---|---|---|---|---|---|---|---|---|---|---|---|---|---|
| Time | Pressure psi | Top Temperature °C. | Bottom Temperature °C. | ABE Flow g/min | DME Flow g/min | RAF Flow g/min | Extract Flow g/min | DME Drive Hz | ABE Drive Hz | Condenser psig | Accumulator psig | Heater Temperature °C. | Chiller Temperature °C. |
| 10 | 115 | 37.1 | 23.8 | 172 | 171 | 244 | 122 | 21.3 | 38.9 | 80 | 80 | 45 | 9.6 |
| 15 | 116 | 37.5 | 24.2 | 184 | 164 | 236 | 122 | 21.3 | 38.9 | 80 | 80 | 46 | 9.8 |
| 20 | 115 | 37.7 | 24.5 | 191 | 171 | 255 | 122 | 21.3 | 38.9 | 80 | 80 | 46 | 10.0 |
| 25 | 118 | 37.2 | 26.2 | 160 | 137 | 232 | 63 | 23.1 | 39.3 | 77 | 77 | 47 | 10.2 |
| 30 | 122 | 37.6 | 25.5 | 172 | 164 | 232 | 115 | 23.8 | 40.0 | 75 | 75 | 48 | 10.0 |
| 35 | 127 | 37.7 | 25.6 | 172 | 154 | 244 | 105 | 24.6 | 40.6 | 75 | 75 | 48 | 10.0 |
| Average | 117 | 36.9 | 24.1 | 175 | 157 | 236 | 112 | 23.0 | 39.0 | 74 | 74 | 46 | 10.0 |

Sample Analysis.

Extract and raffinate samples were collected at five minute intervals during the CCC testing. The samples were analyzed by gas chromatograph (GC) for acetone, butanol and ethanol content. The extract compositions are summarized in Table 13.

The extract samples were diluted with distilled water to create a single phase and homogenous sample prior to GC. The dilution factor was then used to correct the GC measurements for concentrations prior to dilution.

Table 13 documents the composition of the extract samples as well as information regarding the flow rates and timing that each sample was taken during the run. There are two concentrations reported in the tables. The higher concentrations are for the samples collected after the DME had been evaporated. The lower concentrations are adjusted for what the actual concentration would have been if the DME had not been evaporated. This concentration is relevant as it enables the calculation of the height equivalent of a theoretical stage (HETS) for the extraction column. The extract sample compositions were calculated on a DME free basis (as collected) and calculated to adjust for DME content prior to evaporating solvent.

TABLE 13

Summary of Sample Collection Conditions and Composition of Extract Samples from Continuous Countercurrent Column Run

| | | Flow Rates | | | | | Sample Concentrations (DME Free Basis) | | |
|---|---|---|---|---|---|---|---|---|---|
| Sample | Approximate Sample Collect Time (min) | ABE Flow g/min | DME Flow g/min | RAF Flow g/min | Extract Flow g/min | DME free Sample Collection Flow Rate g/min | Butanol Concentration in Extract Samples, wt. % | Ethanol Concentration in Extract Samples, wt. % | Acetone Concentration in Extract Samples, wt. % |
| 8/5 EXT1 | 5 | 172 | 137 | 205 | 132 | 16.1 | 14.16% | 1.95% | 0.38% |
| 8/5 EXT2 | 11 | 172 | 171 | 244 | 122 | 15.0 | 16.78% | 2.30% | 0.53% |
| 8/5 EXT3 | 15 | 184 | 164 | 236 | 122 | 16.7 | 16.94% | 2.39% | 0.53% |
| 8/5 EXT4 | 20 | 191 | 171 | 255 | 122 | 18.3 | 19.24% | 2.68% | 0.72% |
| 8/5 EXT5 | 26 | 160 | 137 | 232 | 63 | 14.7 | 20.13% | 2.48% | 0.73% |
| 8/5 EXT6 | 30 | 172 | 164 | 232 | 115 | 15.4 | 19.28% | 2.23% | 0.64% |
| 8/5 EXT7 | 35 | 172 | 154 | 244 | 105 | 16.2 | 16.48% | 1.91% | 0.55% |
| Average | Average | 175 | 157 | 236 | 112 | 16.0 | 17.57% | 2.28% | 0.58% |

| | Sample Concentrations (DME Included) | | | Component Mass Balance | | |
|---|---|---|---|---|---|---|
| Sample | Butanol Extract Concentration wt. % | Ethanol Extract Concentration wt. % | Acetone Extract Concentration wt. % | Butanal in-out, as % of in | Ethanol in-out, as % of in | Acetone in-out, as % of in |
| 8/5 EXT1 | 1.7% | 0.2% | 0.0% | 23% | 36% | 95% |
| 8/5 EXT2 | 2.1% | 0.3% | 0.1% | 15% | 27% | 83% |
| 8/5 EXT3 | 2.3% | 0.3% | 0.1% | 11% | 22% | 80% |
| 8/5 EXT4 | 2.9% | 0.4% | 0.1% | -4% | 25% | 85% |
| 8/5 EXT5 | 4.7% | 0.6% | 0.2% | -6% | 2% | 62% |
| 8/5 EXT6 | 2.6% | 0.3% | 0.1% | 2% | 22% | 78% |
| 8/5 EXT7 | 2.6% | 0.3% | 0.1% | 11% | 27% | 75% |
| Average | 2.7% | 0.3% | 0.1% | 7.6% | 23.0% | 79.6% |

Table 14 shows the composition of the raffinate samples. For all samples the concentration of butanol was less than 0.07 wt. %. This is a high degree of recovery and implies that the column is the equivalent of several theoretical equilibrium stages.

TABLE 14

ABE Concentrations in Raffinate Samples

| Sample | Approximate Sample Collection Time | Butanol Concentration by GC, wt % | Ethanol Concentration by GC, wt % | Acetone Concentration by GC, wt % | RAF Flow, g/min |
|---|---|---|---|---|---|
| 8/5 RAF-1 | 5 | 0.06% | 0.15% | 0.01% | 157 |
| 8/5 RAF-2 | 11 | 0.07% | 0.18% | 0.03% | 157 |
| 8/5 RAF-3 | 15 | 0.07% | 0.20% | 0.04% | 157 |
| 8/5 RAF-4 | 20 | 0.04% | 0.14% | 0.03% | 157 |
| 8/5 RAF-5 | 26 | 0.06% | 0.27% | 0.06% | 157 |
| 8/5 RAF-6 | 30 | 0.04% | 0.21% | 0.04% | 157 |
| 8/5 RAF-7 | 35 | 0.04% | 0.20% | 0.05% | 157 |

*The butanol concentration in all the raffinate samples is below 0.1 wt. % indicating a high degree of extraction.

The operating conditions presented in Table 12 show small variation in process flow rates. For this reason the data collected is representative of what is to be expected for stable operation. The mass balance on butanol presented in Table 13 is also an indication that the sample analysis accurate as there is only a 7.6% deviation from a perfect mass balance on n-butanol.

The extract samples had an average butanol concentration of 17.6 wt. %. This is well above the solubility limit for butanol in water which resulted in the formation of a butanol rich liquid phase. The butanol phase was found to be approximately 80 wt. % butanol and can be decanted from the aqueous layer.

Conclusion.

A lab scale counter current column was constructed to extract acetone, butanol and ethanol from dilute aqueous solution. The feed concentration was 0.2 wt. % acetone, 1.8 wt. % butanol and 0.5 wt. % ethanol. Dimethyl ether was used to extract the ABE from the dilute aqueous solution and concentrate it in an extract stream. The lab scale extraction column proved that a 1.8 wt. % butanol mixture can be concentrated well above the solubility limit of butanol in water. The end result was demonstration of an extraction process that can take a dilute butanol mixture from 1.8 wt. % butanol to 80 wt. % butanol.

Example 6

Three Different Runs of the Continuous Countercurrent Column (CCC) Runs with Fermentation Broth from *Clostridium acetobutylicum*

This example describes three different runs of the CCC with fermentation broth from *Clostridium acetobutylicum*. The CCC of Example 5 was further run using a feed derived from actual fermentation broth from *Clostridium acetobutylicum*. The fermentation was intentionally interrupted prior to completion. The solvent and other metabolic products are well below the levels that would be toxic to the organism.

The CCC apparatus used is described in detail in Example 5. The extraction column operated at room temperature (~25° C.) throughout the column. Periodic extract and raffinate samples were taken and analyzed for the constituents in the extract and raffinate discharges.

This example describes three different runs. In all cases, the mass of solvent to the mass of feed ratio (S/F) was 0.9. In all example the fermentation broth was first centrifuged to removal all cellular matter. Thus, the feed solution was clarified. In the case of the first run, the following components were measured via gas chromatograph (GC) analysis using external standard calibration. The external standard was run prior to analyzing the samples to provide individual calibration between peak area and the respective constituent under measure. The biomolecular constituents measured were: acetone, ethanol, n-butanol, isobutanol, acetoin, acetate, and butyrate. Acetate was the conjugate base of acetic acid. Butyrate was the conjugate base of butyric acid. All components were quantified in the extract and raffinate. Since the extract and raffinate are mostly water and DME dissolves in water to approximately 20 wt. %, the samples were allowed to degas over a 24 hour period. Based on the GC peak measurement for DME, this waiting period resulted in a reduction in dissolved DME of over two orders of magnitude in samples. Samples were, effectively, solvent free at the time of GC analysis.

In the first run, the feedstock or feed solution was comprised of:
1.95 g/L (0.195 wt. %) acetone,
0.32 g/L (0.032 wt. %) ethanol
3.96 g/L (0.396 wt. %) n-butanol
0.15 g/L (0.015 wt. %) acetoin
2.26 g/L (0.226 wt. %) acetate
0.67 g/L (0.067 wt. %) butyrate This solution is typical of a fermentation broth in continuous solvent production. The n-butanol level is well below the 1.8 wt. % that would inhibit solvent production and, potentially, be toxic to the organism.

In the second run, the feed solution was identical to the above. Isobutanol was added to the solution. Thus, the feed concentration for all biomolecular constituents other than isobutanol was identical to the first run. Isobutanol concentration was 10.98 g/L (1.098 wt. %).

The third run was taken from a different fermentation run. The fermentation was interrupted prior to completion and the cellular material removed from the solution.

In the third run, the feedstock or feed solution was comprised of:
4.87 g/L (0.487 wt. %) acetone,
0.80 g/L (0.080 wt. %) ethanol
11.65 g/L (1.165 wt. %) isobutanol
9.43 g/L (0.943 wt. %) n-butanol
0.33 g/L (0.033 wt. %) acetoin
5.47 g/L (0.547 wt. %) acetate
1.71 g/L (0.171 wt. %) butyrate Data Collection.

During the run, samples were taken of the extract and raffinate. In the case of the extract, the bulk DME was removed by reduction of pressure and addition of heat to flash the DME from the water and other solution constituents.

Sample Analysis.

Extract and raffinate samples were collected at periodic intervals during the CCC testing. After a twenty-four hour degas period, the samples were analyzed by gas chromatograph (GC) for acetone, ethanol, isobutanol, n-butanol, acetoin, acetate, and butyrate. Glucose was measured via a DNS (3,5-dinitrosalicylic acid) assay. The DNS assay is an aromatic compound that reacts with reducing sugars to form 3-amino-5-nitrosalicylic acid, a compound that strongly absorbs light at 540 nm.

In cases where the extract formed a two phase solution, the extract samples were diluted with distilled water to create a single phase and homogenous sample prior to GC. The dilution factor was then used to correct the GC measurements for concentrations prior to dilution.

Run 1 demonstrated the ability to recover butanol with a distribution coefficient of ~2.5 and that the column was approximately 2 theoretical stages. (This is derived by calculation from the extract and raffinate measurements). It further showed that acetate (conjugate base of acidic acid due to pH being greater than 5.5) was not extracted. About half of the butyrate (conjugate base of butyric acid) was extracted. The results are summarized in Table 15.

TABLE 15

| Sample | Time min | Acetone g/L | Ethanol g/L | n-butanol (N) g/L | Acetoin g/L | Acetate g/L | Butyrate g/L |
|---|---|---|---|---|---|---|---|
| Feed | 0 | 1.95 | 0.32 | 3.96 | 0.15 | 2.26 | 0.67 |
| Extract | 20 | 8.47 | 2.39 | 51.74 | 1.56 | 0.00 | 1.35 |
| Raffinate | 20 | 0.81 | 0.16 | 0.27 | 0.05 | 4.43 | 0.54 |
| Extract | 40 | 12.45 | 15.68 | 57.41 | 1.58 | 0.33 | 1.83 |
| Raffinate | 40 | 0.79 | 0.20 | 0.22 | 0.05 | 4.43 | 0.60 |
| Extract | 90 | 11.93 | 2.59 | 59.43 | 1.69 | 0.31 | 1.81 |
| Raffinate | 90 | 0.92 | 0.23 | 0.33 | 0.08 | 4.32 | 0.70 |

Run 2 demonstrated that the distribution coefficients of isobutanol and butanol are approximately equal. Moreover, a significant portion of the sugar was not extracted. The results of Run 1 for extraction of acetate and butyrate were repeated and confirmed. The ability to avoid extracting the sugar allows for recycling the broth and the feedstock. Sugar reuse/recovery has been a large barrier problem in continuous fermentation. The results are summarized in Table 16.

Run 3 further demonstrated the ability to extract butanols from dilute solution. The column reached steady state at an intermediate point in the run. This resulted in an extract that formed two phases, allowing for large scale and continuous extraction. The phase split material has a high butanol concentration and, thus, can be stripped of water to obtain anhydrous butanol. The results are summarized in Table 17.

TABLE 16

| Sample | Time min | Acetone g/L | Ethanol g/L | Isobutanol (I) g/L | n-butanol (N) g/L | Combined BuOH g/L | Ratio of I/N | Acetoin g/L | Acetate g/L | Butyrate g/L | Glucose g/L |
|---|---|---|---|---|---|---|---|---|---|---|---|
| Feed | 0 | 1.95 | 0.32 | 10.98 | 3.96 | 14.94 | 2.77 | 0.15 | 2.26 | 0.67 | 30.57 |
| Extract | 27 | 2.39 | 0.36 | 19.76 | 8.84 | 28.61 | 2.77 | 0.27 | 0.60 | 0.80 | 1.87 |
| Raffinate | 27 | 0.12 | 0.04 | 0.05 | 0.04 | 0.09 | 2.77 | 0.01 | 0.94 | 0.18 | 17.26 |
| Extract | 34 | 4.64 | 1.07 | 52.13 | 16.54 | 68.66 | 2.77 | 0.54 | 0.00 | 0.71 | 2.23 |
| Raffinate | 34 | 0.15 | 0.05 | 0.05 | 0.05 | 0.10 | 2.77 | 0.02 | 1.50 | 0.22 | 20.38 |
| Extract | 43 | 3.50 | 0.91 | 40.12 | 14.82 | 54.93 | 2.77 | 0.63 | 0.00 | 0.80 | 2.38 |
| Raffinate | 43 | 0.14 | 0.06 | 0.07 | 0.05 | 0.12 | 2.77 | 0.02 | 1.74 | 0.24 | 19.39 |
| Extract | 47 | 4.07 | 1.03 | 48.48 | 18.09 | 66.57 | 2.77 | 0.63 | 0.00 | 0.50 | 2.15 |
| Raffinate | 47 | 0.40 | 0.11 | 0.92 | 0.35 | 1.26 | 2.77 | 0.02 | 2.09 | 0.38 | 23.50 |

TABLE 17

| Sample | Time min | Acetone g/L | Ethanol g/L | Isobutanol (I) g/L | n-butanol (N) g/L | Combined BuOH g/L | Ratio of I/N | Acetoin g/L | Acetate g/L | Butyrate g/L | Glucose g/L |
|---|---|---|---|---|---|---|---|---|---|---|---|
| Feed | 0 | 4.87 | 0.80 | 11.65 | 9.43 | 21.08 | 1.24 | 0.33 | 5.47 | 1.71 | 48.47 |
| Extract | 22 | 2.98 | 1.13 | 18.65 | 19.10 | 37.75 | 0.98 | 0.96 | 0.41 | 3.52 | 1.46 |
| Raffinate | 22 | 1.20 | 0.34 | 2.72 | 2.04 | 4.76 | 1.34 | 0.07 | 6.78 | 50.78 | 1.39 |
| Extract | 27 | 5.30 | 1.53 | 35.80 | 32.63 | 68.43 | 1.10 | 1.00 | 0.00 | 9.29 | 1.44 |
| Raffinate | 27 | 0.40 | 0.40 | 0.38 | 0.32 | 0.70 | 1.22 | 0.00 | 5.37 | 19.52 | 0.95 |
| Extract Bot | 31 | 7.88 | 2.29 | 39.30 | 33.91 | 73.21 | 1.16 | 1.64 | 0.48 | 1.57 | 4.74 |
| Extract Top | 31 | 7.03 | 1.98 | 316.67 | 304.97 | 621.64 | 1.04 | 0.91 | 0.40 | 22.09 | 0.00 |
| Raffinate | 31 | 0.31 | 0.42 | 0.38 | 0.30 | 0.68 | 1.28 | 0.00 | 6.42 | 0.88 | 47.66 |
| Extract Bot | 37 | 7.90 | 2.59 | 39.69 | 34.66 | 74.36 | 1.15 | 1.88 | 0.00 | 1.24 | 5.78 |
| Extract Top | 37 | 6.44 | 2.11 | 328.99 | 318.40 | 647.39 | 1.03 | 1.02 | 0.37 | 22.52 | 0.00 |
| Raffinate | 37 | 0.14 | 0.64 | 0.23 | 0.18 | 0.41 | 1.29 | 0.00 | 6.01 | 0.88 | 41.23 |
| Extract | 43 | 5.14 | 2.11 | 35.34 | 32.95 | 68.29 | 1.07 | 1.83 | 0.48 | 2.21 | 6.20 |
| Raffinate | 43 | 0.15 | 0.89 | 0.23 | 0.16 | 0.40 | 1.42 | 0.00 | 7.11 | 0.88 | 48.87 |
| Extract | 70 | 4.61 | 1.85 | 30.95 | 29.58 | 60.53 | 1.05 | 1.62 | 0.40 | 1.71 | 3.94 |
| Raffinate | 70 | 0.11 | 1.56 | 0.43 | 0.31 | 0.74 | 1.37 | 0.00 | 6.84 | 0.95 | 42.10 |
| Extract | 74 | 4.09 | 1.71 | 31.83 | 31.10 | 62.93 | 1.02 | 1.46 | 0.00 | 1.38 | 3.87 |
| Raffinate | 74 | 0.60 | 0.71 | 0.48 | 0.33 | 0.81 | 1.45 | 0.00 | 7.77 | 0.97 | 44.36 |
| Extract | 78 | 3.83 | 1.70 | 33.19 | 32.83 | 66.02 | 1.01 | 1.60 | 0.55 | 3.01 | 4.81 |
| Raffinate | 78 | 0.82 | 0.24 | 0.48 | 0.34 | 0.82 | 1.41 | 0.06 | 7.07 | 0.87 | 48.18 |
| Extract | 82 | 4.63 | 1.92 | 37.48 | 36.64 | 74.12 | 1.02 | 1.65 | 0.40 | 1.88 | 4.95 |
| Raffinate | 82 | 0.46 | 1.14 | 0.48 | 0.34 | 0.82 | 1.44 | 0.00 | 7.29 | 0.93 | 43.14 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An energetically efficient method for concentrating a biomolecule from a dilute biomolecule-water solution comprising:
    a) mixing the dilute biomolecule-water solution with liquid phase dimethyl ether (DME), wherein the distribution coefficient for the biomolecule in a mixture of the DME and the biomolecule-water solution favors the transfer of the biomolecule from the biomolecule-water solution to the DME, thereby yielding a solution comprising a first phase and a second phase, the first phase comprising biomolecule-containing DME and the second phase comprising the dilute biomolecule-water solution, thereby extracting a portion of the biomolecule from the biomolecule-water solution into the DME;
    b) separating the first phase and the second phase;
    c) vaporizing the liquid phase DME in the first phase to vapor phase DME, thereby releasing the biomolecule from the DME, yielding a concentrated biomolecule-water solution;
    d) recovering the vapor phase DME by condensing to liquid phase; and
    e) repeating steps a)-d), wherein the DME recovered in step d) is mixed with the dilute biomolecule-water solution in step a).

2. The method of claim 1, wherein at least about 1 million gallons dilute biomolecule-water solution annually are processed.

3. The method of claim 1, wherein the feedstock dilute biomolecule-water solution comprises from about 0.1 wt. % to about 10.0 wt. % biomolecule.

4. The method of claim 1, wherein the biomolecule is one or more C3-C5 carboxylic acids or dicarboxylic acids.

5. The method of claim 1, wherein the biomolecule is one or more C1-C18 dicarboxylic acids.

6. The method of claim 5, wherein the one or more C1-C18 dicarboxylic acids are selected from the group consisting of propanedioic, butanedioic, pentanedioic, hexanedioic, heptanedioic, octanedioic, nonanedioic, decanedioic, undecanedioic, and dodecanedioic (DDDA).

7. The method of claim 1, wherein the biomolecule is one or more C1-C18 fatty alcohols.

8. The method of claim 7, wherein the one or more C1-C18 fatty alcohols are selected from the group consisting of capryl alcohol (1-octanol), 2-ethyl hexanol, pelargonic alcohol (1-nonanol), capric alcohol (1-decanol, decyl alcohol), undecyl alcohol (1 undecanol, undecanol, hendecanol), lauryl alcohol (dodecanol, 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), palmitoleyl alcohol (cis-9-hexadecen-1-ol), heptadecyl alcohol (1-n-heptadecanol, heptadecanol) and stearyl alcohol (1-octadecanol).

9. The method of claim 1, wherein the biomolecule is one or more butanediols.

10. The method of claim 9, wherein the one or more butanediols are selected from 1,4-butanediol and 2,3-butanediol.

11. The method of claim 1, wherein the biomolecule is one or more butadienes.

12. The method of claim 11, wherein the one or more butadienes are selected from the group consisting of butadiene and 2-methyl-1,3-butadiene (isoprene).

13. The method of claim 1, wherein the biomolecule is one or more furfurals.

14. The method of claim 13, wherein the one or more furfurals are selected from the group consisting of furfural and hydroxymethylfurfural (5-(hydroxymethyl)-2-furaldehyde).

15. The method of claim 1, wherein the biomolecule is acetoin and/or furan.

16. The method of claim 1, wherein the biomolecule is a mixture of acetone, butanol and ethanol (ABE).

17. The method of claim 1, wherein the biomolecule has a solubility in water of less than about 15 wt. % at 25° C.

18. The method of claim 1, wherein the biomolecule has a carbon atom number to hydroxyl group ratio of 3 or greater.

19. The method of claim 1, wherein carbohydrates, amino acids and nucleic acids are substantially not extracted.

20. The method of claim 1, wherein the biomolecule is concentrated at least 2-fold.

* * * * *